(12) United States Patent  
Reiter

(10) Patent No.: US 10,504,338 B2  
(45) Date of Patent: *Dec. 10, 2019

(54) METHOD AND APPARATUS FOR ALERT VALIDATION

(71) Applicant: ARRIA DATA2TEXT LIMITED, Aberdeen (GB)

(72) Inventor: Ehud B. Reiter, Aberdeen (GB)

(73) Assignee: Arria Data2Text Limited, Aberdeen (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/009,006

(22) Filed: Jun. 14, 2018

(65) Prior Publication Data

US 2019/0035232 A1 Jan. 31, 2019

Related U.S. Application Data

(63) Continuation of application No. 15/421,921, filed on Feb. 1, 2017, now Pat. No. 10,026,274, which is a (Continued)

(51) Int. Cl.
*G08B 5/36* (2006.01)
*G08B 5/22* (2006.01)
(Continued)

(52) U.S. Cl.
CPC ........... *G08B 5/36* (2013.01); *G06F 17/2247* (2013.01); *G06F 17/248* (2013.01); *G06F 17/27* (2013.01);
(Continued)

(58) Field of Classification Search
CPC . G08B 5/36; G06F 17/27; G06F 19/30; G06F 19/3487
(Continued)

(56) References Cited

U.S. PATENT DOCUMENTS 5,181,250 A 1/1993 Morgan et al.
5,237,502 A 8/1993 White et al.
(Continued)

FOREIGN PATENT DOCUMENTS

AU 2011247830 B2 12/2011
AU 2011253627 B2 12/2011
(Continued)

OTHER PUBLICATIONS

Alawneh et al., "Pattern Recognition Techniques Applied to the Abstraction of Traces of Inter-Process Communication," Software Maintenance and Reengineering (CSMR), 2011 15th European Conference on Year: 2011, IEEE Conference Publications, pp. 211-220, (2011).

(Continued)

*Primary Examiner* — John A Tweel, Jr.
(74) *Attorney, Agent, or Firm* — Alston & Bird LLP

(57) ABSTRACT

Methods, apparatuses, and computer program products are described herein that are configured to enable validation of an alert condition. In some example embodiments, a method is provided that comprises detecting an alert condition. The method of this embodiment may also include generating a set of messages based on one or more key events in a primary data channel and one or more significant events in one or more related data channels in response to the alert condition. The method of this embodiment may also include determining a validity of the alert condition based on the set of messages that express the one or more key events, the one or more significant events, a relationship between the one or more key events and the one or more significant events, an alert context and the one or causes of the alert condition.

16 Claims, 9 Drawing Sheets

Related U.S. Application Data continuation of application No. 14/311,806, filed on Jun. 23, 2014, now Pat. No. 9,640,045, which is a continuation of application No. 14/023,023, filed on Sep. 10, 2013, now Pat. No. 8,762,133, which is a continuation of application No. PCT/US2012/053115, filed on Aug. 30, 2012.

(51) Int. Cl.

| | | |
|---|---|---|
| *G06F 19/00* | (2018.01) | |
| *G06F 17/24* | (2006.01) | |
| *G06F 17/28* | (2006.01) | |
| *G08B 23/00* | (2006.01) | |
| *G06F 17/22* | (2006.01) | |
| *G06F 17/27* | (2006.01) | |
| *G16H 70/00* | (2018.01) | |
| *G16H 50/30* | (2018.01) | |
| *G16H 50/70* | (2018.01) | |
| *G16H 50/20* | (2018.01) | |
| *G08B 7/06* | (2006.01) | |
| *G08B 21/04* | (2006.01) | |
| *G08B 29/18* | (2006.01) | |
| *G16H 15/00* | (2018.01) | |

(52) U.S. Cl.
CPC .......... *G06F 17/2881* (2013.01); *G06F 19/00* (2013.01); *G06F 19/30* (2013.01); *G08B 5/22* (2013.01); *G08B 23/00* (2013.01); *G16H 50/20* (2018.01); *G16H 50/30* (2018.01); *G16H 50/70* (2018.01); *G16H 70/00* (2018.01); *G08B 7/06* (2013.01); *G08B 21/0453* (2013.01); *G08B 29/18* (2013.01); *G16H 15/00* (2018.01)

(58) Field of Classification Search
USPC ...................................... 340/691.6
See application file for complete search history.

(56) References Cited

U.S. PATENT DOCUMENTS

| | | | |
|---|---|---|---|
| 5,311,429 A | 5/1994 | Tominaga | |
| 5,321,608 A | 6/1994 | Namba et al. | |
| 5,629,687 A | 5/1997 | Sutton et al. | |
| 5,794,177 A | 8/1998 | Carus et al. | |
| 5,802,488 A | 9/1998 | Edatsune | |
| 6,023,669 A | 2/2000 | Suda et al. | |
| 6,078,914 A | 6/2000 | Redfern | |
| 6,138,087 A | 10/2000 | Budzinski | |
| 6,266,617 B1 | 7/2001 | Evans | |
| 6,442,485 B2 | 8/2002 | Evans | |
| 6,466,899 B1 | 10/2002 | Yano et al. | |
| 6,665,640 B1 | 12/2003 | Bennett et al. | |
| 6,717,513 B1 | 4/2004 | Sandelman et al. | |
| 6,947,885 B2 | 9/2005 | Bangalore et al. | |
| 7,043,420 B2 | 5/2006 | Ratnaparkhi | |
| 7,167,824 B2 | 1/2007 | Kallulli | |
| 7,231,341 B2 | 6/2007 | Bangalore et al. | |
| 7,238,313 B2 | 7/2007 | Ferencz et al. | |
| 7,305,336 B2 | 12/2007 | Polanyi et al. | |
| 7,310,969 B2 | 12/2007 | Dale | |
| 7,346,493 B2 | 3/2008 | Ringger et al. | |
| 7,418,447 B2 | 8/2008 | Caldwell et al. | |
| 7,424,363 B2 | 9/2008 | Cheng et al. | |
| 7,444,287 B2* | 10/2008 | Claudatos .......... G08B 13/1672 348/143 |
| 7,496,621 B2 | 2/2009 | Pan et al. | |
| 7,526,424 B2 | 4/2009 | Corston-Oliver et al. | |
| 7,533,089 B2 | 5/2009 | Pan et al. | |
| 7,562,005 B1 | 7/2009 | Bangalore et al. | |
| 7,684,991 B2 | 3/2010 | Stohr et al. | |
| 7,711,581 B2 | 5/2010 | Hood et al. | |
| 7,783,486 B2 | 8/2010 | Rosser et al. | |
| 7,809,552 B2 | 10/2010 | Pan et al. | |
| 7,849,048 B2 | 12/2010 | Langseth et al. | |
| 7,849,049 B2 | 12/2010 | Langseth et al. | |
| 7,856,390 B2 | 12/2010 | Schiller | |
| 7,873,509 B1 | 1/2011 | Budzinski | |
| 7,921,091 B2 | 4/2011 | Cox et al. | |
| 7,930,169 B2 | 4/2011 | Billerey-Mosier | |
| 7,933,774 B1 | 4/2011 | Begeja et al. | |
| 7,966,172 B2 | 6/2011 | Ruiz et al. | |
| 7,970,601 B2 | 6/2011 | Burmester et al. | |
| 7,979,267 B2 | 7/2011 | Ruiz et al. | |
| 8,019,610 B2 | 9/2011 | Walker et al. | |
| 8,024,331 B2 | 9/2011 | Calistri-Yeh et al. | |
| 8,037,000 B2 | 10/2011 | Delmonico et al. | |
| 8,082,144 B1 | 12/2011 | Brown et al. | |
| 8,090,727 B2 | 1/2012 | Lachtarnik et al. | |
| 8,150,676 B1 | 4/2012 | Kaeser | |
| 8,175,873 B2 | 5/2012 | Di Fabbrizio et al. | |
| 8,180,647 B2 | 5/2012 | Walker et al. | |
| 8,180,758 B1 | 5/2012 | Cornali | |
| 8,229,937 B2 | 7/2012 | Kiefer et al. | |
| 8,355,903 B1 | 1/2013 | Birnbaum et al. | |
| 8,374,848 B1 | 2/2013 | Birnbaum et al. | |
| 8,425,325 B2 | 4/2013 | Hope | |
| 8,473,911 B1 | 6/2013 | Baxter | |
| 8,494,944 B2 | 7/2013 | Schiller | |
| 8,515,733 B2 | 8/2013 | Jansen | |
| 8,515,737 B2 | 8/2013 | Allen | |
| 8,548,814 B2 | 10/2013 | Manuel-Devadoss | |
| 8,548,915 B2 | 10/2013 | Antebi et al. | |
| 8,561,014 B2 | 10/2013 | Mengusoglu et al. | |
| 8,566,090 B2 | 10/2013 | Di Fabbrizio et al. | |
| 8,589,148 B2 | 11/2013 | Atallah et al. | |
| 8,589,172 B2 | 11/2013 | Alonso et al. | |
| 8,616,896 B2 | 12/2013 | Lennox | |
| 8,620,669 B2 | 12/2013 | Walker et al. | |
| 8,626,613 B2 | 1/2014 | Dale et al. | |
| 8,630,844 B1 | 1/2014 | Nichols et al. | |
| 8,655,889 B2 | 2/2014 | Hua et al. | |
| 8,676,691 B2 | 3/2014 | Schiller | |
| 8,688,434 B1 | 4/2014 | Birnbaum et al. | |
| 8,700,396 B1 | 4/2014 | Mengibar et al. | |
| 8,738,384 B1 | 5/2014 | Bansal et al. | |
| 8,738,558 B2 | 5/2014 | Antebi et al. | |
| 8,762,134 B2 | 5/2014 | Reiter | |
| 8,762,133 B2* | 6/2014 | Reiter ............ G08B 5/22 704/9 |
| 8,775,161 B1 | 7/2014 | Nichols et al. | |
| 8,825,533 B2 | 9/2014 | Basson et al. | |
| 8,843,363 B2 | 9/2014 | Birnbaum et al. | |
| 8,849,670 B2 | 9/2014 | Di Cristo et al. | |
| 8,886,520 B1 | 11/2014 | Nichols et al. | |
| 8,892,417 B1 | 11/2014 | Nichols et al. | |
| 8,892,419 B2 | 11/2014 | Lundberg et al. | |
| 8,898,063 B1 | 11/2014 | Sykes et al. | |
| 8,903,711 B2 | 12/2014 | Lundberg et al. | |
| 8,903,718 B2 | 12/2014 | Akuwudike | |
| 8,909,595 B2 | 12/2014 | Gandy et al. | |
| 8,914,452 B2 | 12/2014 | Boston et al. | |
| 8,924,330 B2 | 12/2014 | Antebi et al. | |
| 8,930,305 B2 | 1/2015 | Namburu et al. | |
| 8,977,953 B1 | 3/2015 | Pierre et al. | |
| 8,984,051 B2 | 3/2015 | Olsen et al. | |
| 9,002,695 B2 | 4/2015 | Watanabe et al. | |
| 9,002,869 B2 | 4/2015 | Riezler et al. | |
| 9,015,730 B1 | 4/2015 | Allen et al. | |
| 9,028,260 B2 | 5/2015 | Nanjiani et al. | |
| 9,092,276 B2 | 7/2015 | Allen et al. | |
| 9,104,720 B2 | 8/2015 | Rakshit et al. | |
| 9,110,882 B2 | 8/2015 | Overell et al. | |
| 9,110,977 B1 | 8/2015 | Pierre et al. | |
| 9,111,534 B1 | 8/2015 | Sylvester et al. | |
| 9,135,244 B2 | 9/2015 | Reiter | |
| 9,135,662 B2 | 9/2015 | Evenhouse et al. | |
| 9,146,904 B2 | 9/2015 | Allen | |
| 9,164,982 B1 | 10/2015 | Kaeser | |
| 9,190,054 B1 | 11/2015 | Riley et al. | |
| 9,208,147 B1 | 12/2015 | Nichols et al. | |

(56) References Cited

U.S. PATENT DOCUMENTS

| | | |
|---|---|---|
| 9,229,927 B2 | 1/2016 | Wolfram et al. |
| 9,240,197 B2 | 1/2016 | Begeja et al. |
| 9,244,894 B1 | 1/2016 | Dale et al. |
| 9,251,134 B2 | 2/2016 | Birnbaum et al. |
| 9,251,143 B2 | 2/2016 | Bird et al. |
| 9,263,039 B2 | 2/2016 | Di Cristo et al. |
| 9,268,770 B1 | 2/2016 | Kursun |
| 9,323,743 B2 | 4/2016 | Reiter |
| 9,405,448 B2 | 8/2016 | Reiter |
| 9,600,471 B2 | 3/2017 | Bradshaw et al. |
| 9,640,045 B2 * | 5/2017 | Reiter .................. G08B 5/22 |
| 9,990,360 B2 | 6/2018 | Sripada |
| 10,026,274 B2 * | 7/2018 | Reiter .................. G08B 5/22 |
| 10,115,202 B2 | 10/2018 | Sripada |
| 2002/0026306 A1 | 2/2002 | Bangalore et al. |
| 2003/0131315 A1 | 7/2003 | Escher |
| 2003/0212545 A1 | 11/2003 | Kallulli |
| 2004/0246120 A1 * | 12/2004 | Benner ............. H04N 1/00204 340/506 |
| 2005/0039107 A1 | 2/2005 | Hander et al. |
| 2005/0228635 A1 | 10/2005 | Araki et al. |
| 2005/0256703 A1 | 11/2005 | Markel |
| 2006/0085667 A1 | 4/2006 | Kubota et al. |
| 2006/0178868 A1 | 8/2006 | Billerey-Mosier |
| 2006/0259293 A1 | 11/2006 | Orwant |
| 2007/0078655 A1 | 4/2007 | Semkow et al. |
| 2007/0106628 A1 | 5/2007 | Adjali et al. |
| 2007/0129942 A1 | 6/2007 | Ban et al. |
| 2007/0143099 A1 | 6/2007 | Balchandran et al. |
| 2008/0221865 A1 | 9/2008 | Wellmann |
| 2008/0221870 A1 | 9/2008 | Attardi et al. |
| 2008/0281781 A1 | 11/2008 | Zhao et al. |
| 2008/0312954 A1 | 12/2008 | Ullrich et al. |
| 2009/0089100 A1 | 4/2009 | Nenov et al. |
| 2009/0089126 A1 | 4/2009 | Odubiyi |
| 2009/0111486 A1 | 4/2009 | Burstrom |
| 2009/0156229 A1 | 6/2009 | Hein et al. |
| 2009/0198496 A1 | 8/2009 | Denecke |
| 2009/0281839 A1 * | 11/2009 | Lynn .................. G06F 19/321 705/3 |
| 2009/0286514 A1 | 11/2009 | Lichorowic et al. |
| 2009/0287567 A1 | 11/2009 | Penberthy et al. |
| 2010/0146491 A1 | 6/2010 | Hirano et al. |
| 2010/0153095 A1 | 6/2010 | Yang et al. |
| 2010/0174545 A1 | 7/2010 | Otani |
| 2010/0191658 A1 | 7/2010 | Kannan et al. |
| 2010/0203970 A1 | 8/2010 | Hope |
| 2010/0332235 A1 | 12/2010 | David |
| 2011/0010164 A1 | 1/2011 | Williams |
| 2011/0068929 A1 * | 3/2011 | Franz ................ A61B 5/02055 340/573.1 |
| 2011/0087486 A1 | 4/2011 | Schiller |
| 2011/0160986 A1 | 6/2011 | Wu et al. |
| 2011/0179006 A1 | 7/2011 | Cox et al. |
| 2011/0218822 A1 | 9/2011 | Buisman et al. |
| 2011/0225185 A1 * | 9/2011 | Gupta ............... G06F 17/30067 707/769 |
| 2011/0257839 A1 | 10/2011 | Mukherjee |
| 2012/0078888 A1 | 3/2012 | Brown et al. |
| 2012/0084027 A1 | 4/2012 | Caine |
| 2012/0136649 A1 | 5/2012 | Freising et al. |
| 2012/0158089 A1 * | 6/2012 | Bocek .................. A61N 1/37 607/28 |
| 2012/0173475 A1 | 7/2012 | Ash et al. |
| 2012/0290289 A1 | 11/2012 | Manera et al. |
| 2012/0310990 A1 | 12/2012 | Viegas et al. |
| 2013/0030810 A1 | 1/2013 | Kopparapu et al. |
| 2013/0066873 A1 | 3/2013 | Salvetti et al. |
| 2013/0144606 A1 | 6/2013 | Birnbaum et al. |
| 2013/0145242 A1 | 6/2013 | Birnbaum et al. |
| 2013/0151238 A1 | 6/2013 | Beaurpere et al. |
| 2013/0174026 A1 | 7/2013 | Locke |
| 2013/0185050 A1 | 7/2013 | Bird et al. |
| 2013/0211855 A1 | 8/2013 | Eberle et al. |
| 2013/0238329 A1 | 9/2013 | Casella dos Santos |
| 2013/0238330 A1 | 9/2013 | Casella dos Santos |
| 2013/0238987 A1 | 9/2013 | Lutwyche |
| 2013/0251233 A1 | 9/2013 | Yang et al. |
| 2013/0268263 A1 | 10/2013 | Park et al. |
| 2013/0293363 A1 | 11/2013 | Plymouth et al. |
| 2013/0311201 A1 | 11/2013 | Chatfield et al. |
| 2014/0019531 A1 | 1/2014 | Czajka et al. |
| 2014/0025371 A1 | 1/2014 | Min |
| 2014/0039878 A1 | 2/2014 | Wasson |
| 2014/0052696 A1 | 2/2014 | Soroushian |
| 2014/0062712 A1 | 3/2014 | Reiter |
| 2014/0067377 A1 | 3/2014 | Reiter |
| 2014/0072947 A1 | 3/2014 | Boguraev et al. |
| 2014/0072948 A1 | 3/2014 | Boguraev et al. |
| 2014/0089212 A1 | 3/2014 | Sbodio |
| 2014/0100846 A1 | 4/2014 | Haine et al. |
| 2014/0100901 A1 | 4/2014 | Haine et al. |
| 2014/0100923 A1 | 4/2014 | Strezo et al. |
| 2014/0143720 A1 | 5/2014 | Dimarco et al. |
| 2014/0149107 A1 | 5/2014 | Schilder |
| 2014/0164303 A1 | 6/2014 | Bagchi et al. |
| 2014/0164304 A1 | 6/2014 | Bagchi et al. |
| 2014/0188477 A1 | 7/2014 | Zhang |
| 2014/0278358 A1 | 9/2014 | Byron et al. |
| 2014/0281935 A1 | 9/2014 | Byron et al. |
| 2014/0281951 A1 | 9/2014 | Megiddo et al. |
| 2014/0297268 A1 | 10/2014 | Govrin et al. |
| 2014/0316768 A1 | 10/2014 | Khandekar |
| 2014/0375466 A1 | 12/2014 | Reiter |
| 2014/0379322 A1 | 12/2014 | Koutrika et al. |
| 2014/0379378 A1 | 12/2014 | Cohen-Solal et al. |
| 2015/0006437 A1 | 1/2015 | Byron et al. |
| 2015/0032443 A1 | 1/2015 | Karov et al. |
| 2015/0081299 A1 | 3/2015 | Jasinschi et al. |
| 2015/0081307 A1 | 3/2015 | Cederstrom et al. |
| 2015/0081321 A1 | 3/2015 | Jain |
| 2015/0095015 A1 | 4/2015 | Lani et al. |
| 2015/0106307 A1 | 4/2015 | Antebi et al. |
| 2015/0142418 A1 | 5/2015 | Byron et al. |
| 2015/0142421 A1 | 5/2015 | Buurman et al. |
| 2015/0154359 A1 | 6/2015 | Harris et al. |
| 2015/0163358 A1 | 6/2015 | Klemm et al. |
| 2015/0169522 A1 | 6/2015 | Logan et al. |
| 2015/0169548 A1 | 6/2015 | Reiter |
| 2015/0169659 A1 | 6/2015 | Lee et al. |
| 2015/0169720 A1 | 6/2015 | Byron et al. |
| 2015/0169737 A1 | 6/2015 | Bryon et al. |
| 2015/0179082 A1 | 6/2015 | Byron et al. |
| 2015/0227508 A1 | 8/2015 | Howald et al. |
| 2015/0242384 A1 | 8/2015 | Reiter |
| 2015/0261744 A1 | 9/2015 | Suenbuel et al. |
| 2015/0261836 A1 | 9/2015 | Madhani et al. |
| 2015/0279348 A1 | 10/2015 | Cao et al. |
| 2015/0310013 A1 | 10/2015 | Allen et al. |
| 2015/0310112 A1 | 10/2015 | Allen et al. |
| 2015/0310861 A1 | 10/2015 | Waltermann et al. |
| 2015/0324343 A1 | 11/2015 | Carter et al. |
| 2015/0324351 A1 | 11/2015 | Sripada et al. |
| 2015/0324374 A1 | 11/2015 | Sripada et al. |
| 2015/0324413 A1 | 11/2015 | Gubin et al. |
| 2015/0326622 A1 | 11/2015 | Carter et al. |
| 2015/0331845 A1 | 11/2015 | Guggilla et al. |
| 2015/0331846 A1 | 11/2015 | Guggilla et al. |
| 2015/0332670 A1 | 11/2015 | Akbacak et al. |
| 2015/0356127 A1 | 12/2015 | Pierre et al. |
| 2015/0363363 A1 | 12/2015 | Bohra et al. |
| 2015/0363364 A1 | 12/2015 | Sripada |
| 2015/0363382 A1 | 12/2015 | Bohra et al. |
| 2015/0363390 A1 | 12/2015 | Mungi et al. |
| 2015/0363391 A1 | 12/2015 | Mungi et al. |
| 2015/0371651 A1 | 12/2015 | Aharoni et al. |
| 2016/0019200 A1 | 1/2016 | Allen |
| 2016/0027125 A1 | 1/2016 | Bryce |
| 2016/0055150 A1 | 2/2016 | Bird et al. |
| 2016/0132489 A1 | 5/2016 | Reiter |
| 2016/0140090 A1 | 5/2016 | Dale et al. |

(56) References Cited

U.S. PATENT DOCUMENTS

| | | | |
|---|---|---|---|
| 2016/0328385 | A1 | 11/2016 | Reiter |
| 2017/0018107 | A1 | 1/2017 | Reiter |

FOREIGN PATENT DOCUMENTS

| | | | |
|---|---|---|---|
| AU | 2013201755 A1 | 9/2013 | |
| AU | 2013338351 A1 | 5/2015 | |
| CA | 2577721 C | 3/2006 | |
| CA | 2826116 C | 3/2006 | |
| CN | 103999081 A | 8/2014 | |
| CN | 104182059 A | 12/2014 | |
| CN | 104881320 A | 9/2015 | |
| EP | 1336955 B1 | 5/2006 | |
| EP | 2707809 A1 | 3/2014 | |
| EP | 2750759 A1 | 7/2014 | |
| EP | 2849103 A2 | 3/2015 | |
| GB | 2518192 A | 3/2015 | |
| JP | 61-221873 A | 10/1986 | |
| JP | 2004-21791 A | 1/2004 | |
| JP | 2014165766 A | 9/2014 | |
| WO | WO 2000/074394 A2 | 12/2000 | |
| WO | WO 2002/031628 A2 | 4/2002 | |
| WO | WO 2002/073449 A1 | 9/2002 | |
| WO | WO 2002/073531 A1 | 9/2002 | |
| WO | WO 2002/031628 A3 | 10/2002 | |
| WO | WO 2006/010044 A2 | 1/2006 | |
| WO | WO 2007/041221 A1 | 4/2007 | |
| WO | WO 2009/014465 A2 | 1/2009 | |
| WO | WO 2010/049925 A2 | 5/2010 | |
| WO | WO 2010/051404 A1 | 5/2010 | |
| WO | WO 2012/071571 A2 | 5/2012 | |
| WO | WO 2013/009613 A1 | 1/2013 | |
| WO | WO 2013/042115 A2 | 3/2013 | |
| WO | WO 2013/042116 A1 | 3/2013 | |
| WO | WO 2013/177280 A1 | 11/2013 | |
| WO | WO 2014/035402 A1 | 3/2014 | |
| WO | WO 2014/098560 A2 | 6/2014 | |
| WO | WO 2014/140977 A1 | 9/2014 | |
| WO | WO 2014/187076 A1 | 11/2014 | |
| WO | WO 2015/028844 A1 | 3/2015 | |
| WO | WO 2015/113301 A1 | 8/2015 | |
| WO | WO 2015/148278 A1 | 10/2015 | |
| WO | WO 2015/159133 A1 | 10/2015 | |
| WO | WO 2015/164253 A1 | 10/2015 | |
| WO | WO 2015/175338 A1 | 11/2015 | |
| WO | WO 2016/004266 A2 | 1/2016 | |

OTHER PUBLICATIONS

Andre et al., "From Visual Data to Multimedia Presentations," Grounding Representations: Integration of Sensory Information in Natural Language Processing, Artificial Intelligence and Neural networks, IEE Colloquium On, pp. 1-3, (1995).

Andre et al., "Natural Language Access to Visual Data: Dealing with Space and Movement," Report 63, German Research Center for Artificial Intelligence (DFKI) SFB 314, Project VITRA, pp. 1-21, (1989).

Barzilay et al.; "Aggregation via Set Partitioning for Natural Language Generation", Proceedings of the Human Language Technology Conference of the North American Chapter of the ACL; pp. 359-366; (2006).

Bhoedjang et al., "Optimizing Distributed Data Structures Using Application-Specific Network Interface Software," Parallel Processing, Proceedings; International Conference on Year: 1998, IEEE Conference Publications, pp. 485-492, (1998).

Cappozzo et al., "Surface-Marker Cluster Design Criteria for 3-D Bone Movement Reconstruction," IEEE Transactions on Biomedical Engineering, 44(12):1165-1174, (1997).

Dalianis et al.; "Aggregation in Natural Language Generation;" Trends in Natural Language Generation, an Artificial Intelligence Perspective; pp. 88-105; (1993).

Dragon et al., "Multi-Scale Clustering of Frame-to-Frame Correspondences for Motion Segmentation," Computer Vision ECCV, Springer Berlin Heidelberg, pp. 445-458, (2012).

Gatt et al.,"From Data to Text in the Neonatal Intensive Care Unit: Using NLG Technology for Decision Support and Information Management," AI Communication, pp. 153-186, (2009).

Gorelov et al., "Search Optimization in Semistructured Databases Using Hierarchy of Document Schemas," Programming and Computer Software, 31 (6):321-331, (2005).

Herzog et al., "Combining Alternatives in the Multimedia Presentation of Decision Support Information for Real-Time Control," IFIP, 15 pages,(1998).

Kottke et al., "Motion Estimation via Cluster Matching," 8180 IEEE Transactions on Pattern Analysis and Machine Intelligence, 16(11):1128-1132, (1994).

Kukich, "Knowledge-Based Report Generation: A Knowledge-Engineering Approach to Natural Language Report Generation," Dissertation to the Interdisciplinary Department of Information Science, University of Pittsburg, 260 pages, (1983).

Leonov et al., "Construction of an Optimal Relational Schema for Storing XML Documents in an RDBMS Without Using DTD/XML Schema," Programming and Computer Software, 30(6):323-336, (2004).

Perry et al., "Automatic Realignment of Data Structures to Improve MPI Performance," Networks (ICN), Ninth International Conference on Year: 2010, IEEE Conference Publications, pp. 42-47, (2010).

Quinlan, "Induction of Decision Trees," Machine Learning, Kluwer Academic Publishers, 1(1):81-106, (1986).

Radev et al.,"Generating Natural Language Summaries from Multiple On-Line Sources," Association of Computational Linguistics, 24(3):469-500, (1998).

Reiter et al., "Building Applied Natural Language Generation Systems," Natural Language Engineering 1 (1), 31 pages, (1995).

Reiter et al.; "Studies in Natural Language Processing—Building Natural Language Generation Systems," Cambridge University Press, (2000).

Reiter, "An Architecture for Data-to-Text Systems," Proceedings of ENLG-2007, pp. 97-104, (2007).

Shaw, "Clause Aggregation Using Linguistic Knowledge;" Proceedings of IWNLG, pp. 138-147, (1998). Retrieved from <http://acl.ldc.upenn.edu/W/W98/W98-1415.pdf>.

Spillner et al., "Algorithms for Dispersed Processing," Utility and Cloud Computing (UC), 204 IEEE/ACM 7th International Conference on Year: 2014, IEEE Conferenced Publications, pp. 914-921, (2014).

Voelz et al., "Rocco: A RoboCup Soccer Commentator System," German Research Center for Artificial Intelligence DFKI GmbH, 11 pages, (1999).

Yu et al., "Choosing the Content of Textual Summaries of Large Time-Series Data Sets," Natural Language Engineering, 13:1-28, (2007).

International Preliminary Report on Patentability for Application No. PCT/IB2012/056513 dated May 19, 2015.

International Preliminary Report on Patentability for Application No. PCT/IB2012/056514 dated May 19, 2015.

International Preliminary Report on Patentability for Application No. PCT/IB2012/057773 dated Jun. 30, 2015.

International Preliminary Report on Patentability for Application No. PCT/IB2012/057774 dated Jun. 30, 2015.

International Preliminary Report on Patentability for Application No. PCT/IB2013/050375 dated Jul. 21, 2015.

International Preliminary Report on Patentability for Application No. PCT/IB2013/058131 dated May 5, 2015.

International Preliminary Report on Patentability for Application No. PCT/IB2014/060846 dated Oct. 18, 2016.

International Preliminary Report on Patentability for Application No. PCT/US2012/053115 dated Mar. 3, 2015.

International Preliminary Report on Patentability for Application No. PCT/US2012/053127 dated Mar. 3, 2015.

International Preliminary Report on Patentability for Application No. PCT/US2012/053128 dated Mar. 3, 2015.

(56) References Cited

OTHER PUBLICATIONS

International Preliminary Report on Patentability for Application No. PCT/US2012/053156 dated Mar. 3, 2015.
International Preliminary Report on Patentability for Application No. PCT/US2012/053183 dated Mar. 3, 2015.
International Preliminary Report on Patentability for Application No. PCT/US2012/061051 dated Mar. 3, 2015.
International Preliminary Report on Patentability for Application No. PCT/US2012/063343 dated May 5, 2015.
International Search Report and Written Opinion for Application No. PCT/IB2012/056513 dated Jun. 26, 2013.
International Search Report and Written Opinion for Application No. PCT/IB2012/056514 dated Jun. 26, 2013.
International Search Report and Written Opinion for Application No. PCT/IB2012/057773 dated Jul. 1, 2013.
International Search Report and Written Opinion for Application No. PCT/IB2012/057774 dated Sep. 20, 2013.
International Search Report and Written Opinion for Application No. PCT/IB2013/050375 dated May 7, 2013.
International Search Report and Written Opinion for Application No. PCT/IB2013/058131 dated Jul. 3, 2014.
International Search Report and Written Opinion for Application No. PCT/IB2014/060846 dated Feb. 4, 2015.
International Search Report and Written Opinion for Application No. PCT/US2012/053115 dated Jul. 24, 2013.
International Search Report and Written Opinion for Application No. PCT/US2012/053127 dated Jul. 24, 2013.
International Search Report and Written Opinion for Application No. PCT/US2012/053128 dated Jun. 27, 2013.
International Search Report and Written Opinion for Application No. PCT/US2012/053156 dated Sep. 26, 2013.
International Search Report and Written Opinion for Application No. PCT/US2012/053183 dated Jun. 4, 2013.
International Search Report and Written Opinion for Application No. PCT/US2012/061051 dated Jul. 24, 2013.
International Search Report and Written Opinion for Application No. PCT/US2012/063343; dated Jan. 15, 2014.
Notice of Allowance for U.S. Appl. No. 14/023,023 dated Apr. 11, 2014.
Notice of Allowance for U.S. Appl. No. 14/023,056 dated Apr. 29, 2014.
Notice of Allowance for U.S. Appl. No. 14/311,806 dated Dec. 28, 2016.
Notice of Allowance for U.S. Appl. No. 14/311,998 dated Dec. 22, 2015.
Notice of Allowance for U.S. Appl. No. 14/311,998 dated Jan. 21, 2016.
Notice of Allowance for U.S. Appl. No. 14/634,035 dated Mar. 30, 2016.
Notice of Allowance for U.S. Appl. No. 15/421,921 dated Mar. 14, 2018.
Office Action for U.S. Appl. No. 14/023,023 dated Mar. 4, 2014.
Office Action for U.S. Appl. No. 14/023,056 dated Nov. 21, 2013.
Office Action for U.S. Appl. No. 14/311,806 dated Jun. 10, 2016.
Office Action for U.S. Appl. No. 14/311,998 dated Feb. 20, 2015.
Office Action for U.S. Appl. No. 14/311,998 dated Oct. 7, 2015.
Office Action for U.S. Appl. No. 14/634,035 dated Aug. 28, 2015.
Office Action for U.S. Appl. No. 14/634,035 dated Dec. 10, 2015.
Office Action for U.S. Appl. No. 14/634,035 dated Mar. 30, 2016.
Office Action for U.S. Appl. No. 15/074,425 dated Feb. 26, 2018.
Office Action for U.S. Appl. No. 15/074,425 dated May 10, 2017.
Office Action for U.S. Appl. No. 15/074,425 dated Nov. 27, 2018.
Office Action for U.S. Appl. No. 15/188,423 dated Jul. 20, 2018.
Office Action for U.S. Appl. No. 15/188,423 dated Oct. 23, 2017.
Office Action for U.S. Appl. No. 15/188,423 dated Oct. 30, 2018.
Office Action for U.S. Appl. No. 15/421,921 dated Sep. 27, 2017.
Statement in accordance with the Notice from the European patent Office dated Oct. 1, 2007 concerning business methods (OJ EPO Nov. 2007, 592-593, (XP002456414) 1 page.
U.S. Appl. No. 12/779,636; entitled "System and Method for Using Data to Automatically Generate a Narrative Story" filed May 13, 2010.
U.S. Appl. No. 13/186,308; entitled "Method and Apparatus for Triggering the Automatic Generation of Narratives" filed Jul. 19, 2011.
U.S. Appl. No. 13/186,329; entitled "Method and Apparatus for Triggering the Automatic Generation of Narratives" filed Jul. 19, 2011.
U.S. Appl. No. 13/186,337; entitled "Method and Apparatus for Triggering the Automatic Generation of Narratives" filed Jul. 19, 2011.
U.S. Appl. No. 13/186,346; entitled "Method and Apparatus for Triggering the Automatic Generation of Narratives" filed Jul. 19, 2011.
U.S. Appl. No. 13/464,635; entitled "Use of Tools and Abstraction in a Configurable and Portable System for Generating Narratives" filed May 4, 2012.
U.S. Appl. No. 13/464,675; entitled "Configurable and Portable System for Generating Narratives" filed May 4, 2012.
U.S. Appl. No. 13/464,716; entitled "Configurable and Portable System for Generating Narratives" filed May 4, 2012.
U.S. Appl. No. 14/023,023; entitled "Method and Apparatus for Alert Validation;" filed Sep. 10, 2013.
U.S. Appl. No. 14/023,056; entitled "Method and Apparatus for Situational Analysis Text Generation;" filed Sep. 10, 2013.
U.S. Appl. No. 14/027,684; entitled "Method, Apparatus, and Computer Program Product for User-Directed Reporting;" filed Sep. 16, 2013.
U.S. Appl. No. 14/027,775; entitled "Method and Apparatus for Interactive Reports;" filed Sep. 16, 2013.
U.S. Appl. No. 14/311,806; entitled Method and Apparatus for Alert Validation; In re: Reiter, filed Jun. 23, 2014.
U.S. Appl. No. 14/311,998, entitled Method and Apparatus for Situational Analysis Text Generation; In re: Reiter; filed Jun. 23, 2014.
U.S. Appl. No. 14/634,035, entitled Method and Apparatus for Annotating a Graphical Output; In re: Reiter; filed Feb. 27, 2015.
U.S. Appl. No. 14/914,461, filed Feb. 25, 2016; In re: Reiter et al., entitled Text Generation From Correlated Alerts.
U.S. Appl. No. 15/022,420, filed Mar. 16, 2016; In re: Mahamood, entitled Method and Apparatus for Document Planning.
U.S. Appl. No. 15/074,425, filed Mar. 18, 2016; In re: Reiter, entitled Method and Apparatus for Situational Analysis Text Generation.
U.S. Appl. No. 15/093,337, filed Apr. 7, 2016; In re: Reiter, entitled Method and Apparatus for Referring Expression Generation.
U.S. Appl. No. 15/093,365, filed Apr. 7, 2016; In re: Logan et al., entitled Method and Apparatus for Updating a Previously Generated Text.
U.S. Appl. No. 15/188,423, filed Jun. 21, 2016; In re: Reiter, entitled Method and Apparatus for Annotating a Graphical Output.
U.S. Appl. No. 15/421,921, filed Feb. 1, 2017; In re: Reiter, entitled Method and Apparatus for Alert Validation.
Notice of Allowance for U.S. Appl. No. 15/188,423 dated Dec. 28, 2018.

* cited by examiner

METHOD AND APPARATUS FOR ALERT VALIDATION

CROSS-REFERENCE TO RELATED APPLICATIONS

This application is a continuation of U.S. application Ser. No. 15/421,921, titled "METHOD AND APPARATUS FOR ALERT VALIDATION," filed Feb. 1, 2017, which is a continuation of and claims priority to U.S. application Ser. No. 14/311,806, titled "METHOD AND APPARATUS FOR ALERT VALIDATION," filed Jun. 23, 2014, which is a continuation of and claims priority to U.S. application Ser. No. 14/023,023, titled "METHOD AND APPARATUS FOR ALERT VALIDATION," filed Sep. 10, 2013, which is a continuation of and claims priority to PCT/US2012/053115, titled "METHOD AND APPARATUS FOR ALERT VALIDATION," filed Aug. 30, 2012, the contents of which are incorporated by reference as if set forth in their entirety herein.

TECHNOLOGICAL FIELD

Embodiments of the present invention relate generally to natural language generation technologies and, more particularly, relate to a method, apparatus, and computer program product for alert validation.

BACKGROUND

In some examples, a natural language generation (NLG) system is configured to transform raw input data that is expressed in a non-linguistic format into a format that can be expressed linguistically, such as through the use of natural language. For example, raw input data may take the form of a value of a stock market index over time and, as such, the raw input data may include data that is suggestive of a time, a duration, a value and/or the like. Therefore, an NLG system may be configured to input the raw input data and output text that linguistically describes the value of the stock market index; for example, "securities markets rose steadily through most of the morning, before sliding downhill late in the day."

Data that is input into a NLG system may be provided in, for example, a recurrent formal structure. The recurrent formal structure may comprise a plurality of individual fields and defined relationships between the plurality of individual fields. For example, the input data may be contained in a spreadsheet or database, presented in a tabulated log message or other defined structure, encoded in a 'knowledge representation' such as the resource description framework (RDF) triples that make up the Semantic Web and/or the like. In some examples, the data may include numerical content, symbolic content or the like. Symbolic content may include, but is not limited to, alphanumeric and other non-numeric character sequences in any character encoding, used to represent arbitrary elements of information. In some examples, the output of the NLG system is text in a natural language (e.g. English, Japanese or Swahili), but may also be in the form of synthesized speech.

BRIEF SUMMARY

Methods, apparatuses, and computer program products are described herein that are configured to enable validation of an alert condition. In some example embodiments, a method is provided that comprises detecting an alert condition. The method of this embodiment may also include generating a set of messages based on one or more key events in a primary data channel and one or more significant events in one or more related data channels in response to the alert condition. The method of this embodiment may also include determining a validity of the alert condition based on the set of messages that express the one or more key events, the one or more significant events, a relationship between the one or more key events and the one or more significant events, an alert context and the one or causes of the alert condition.

BRIEF DESCRIPTION OF THE DRAWINGS

Figure 1:
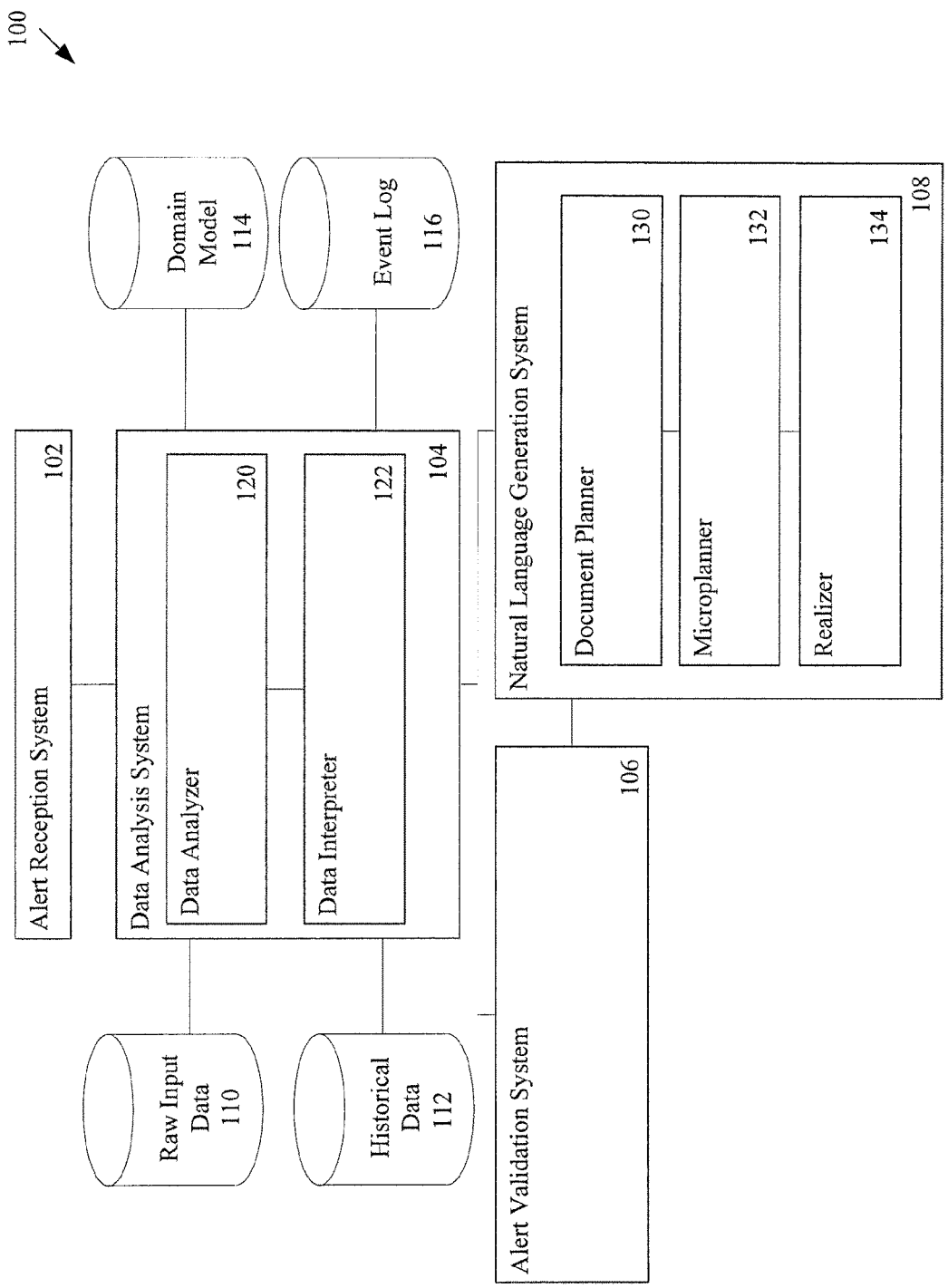
Figure 2A:
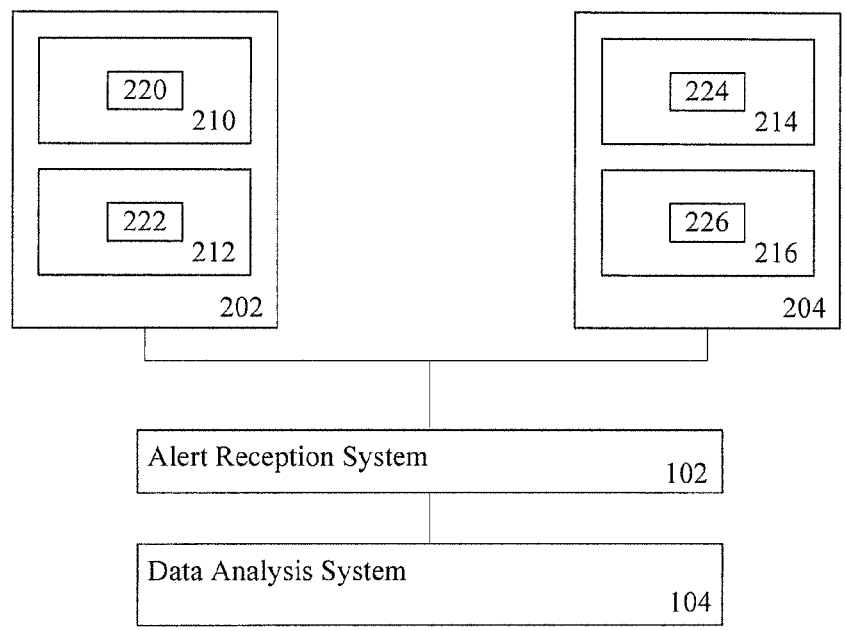
Figure 2B:
Figure 3:
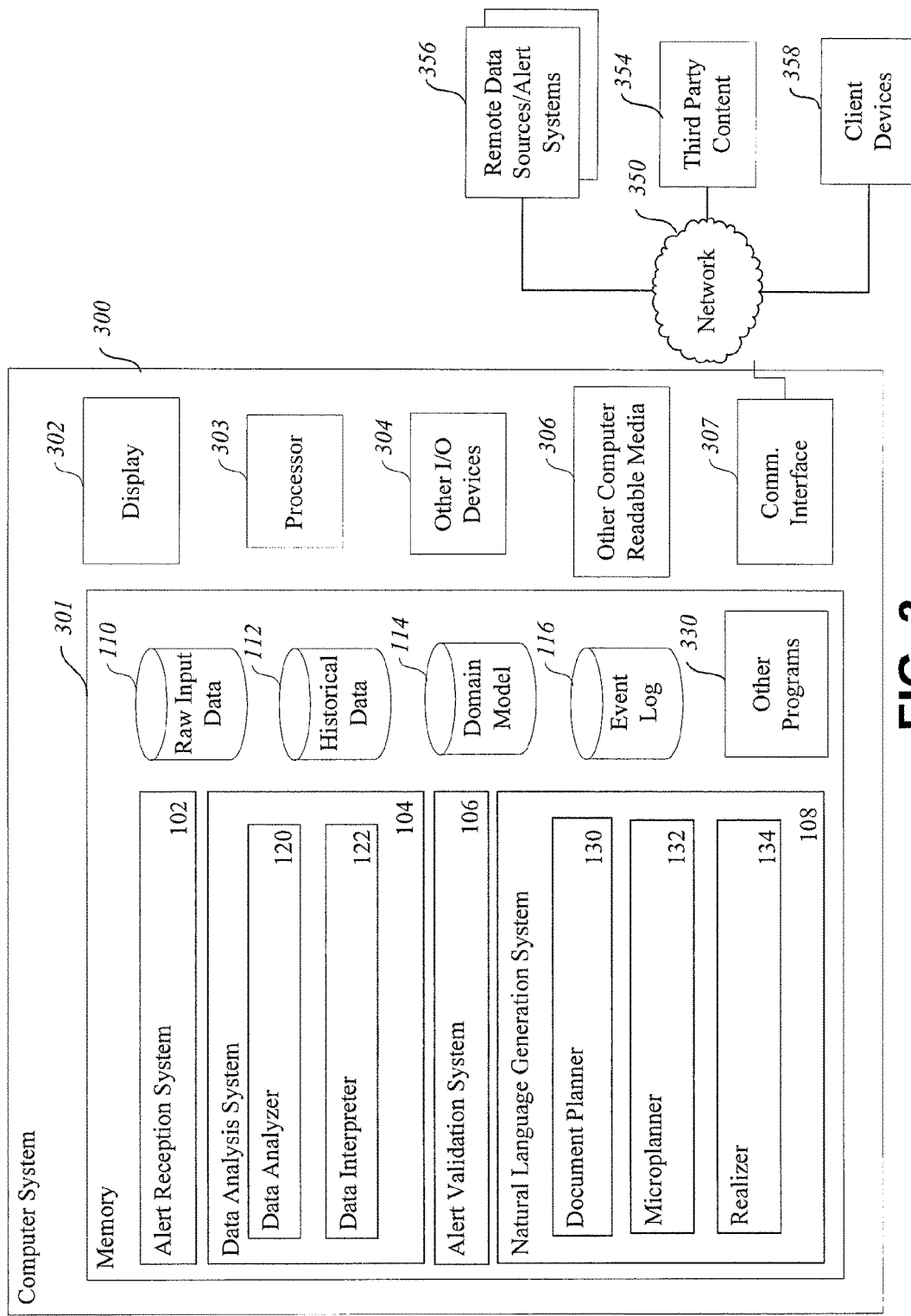

Having thus described embodiments of the invention in general terms, reference will now be made to the accompanying drawings, which are not necessarily drawn to scale, and wherein:

FIG. 1 is a schematic representation of an situational analysis and alert validation system that may benefit from some example embodiments of the present invention;

FIG. 2a illustrates an example alert monitoring system in an example machine monitoring domain according to some example embodiments described herein;

FIG. 2b illustrates an example document plan tree and a text specification in accordance with some example embodiments of the present invention;

FIG. 3 illustrates a block diagram of an apparatus that embodies a situational analysis and alert validation system in accordance with some example embodiments of the present invention; and FIGS. 4-8 illustrate flowcharts that may be performed by a situational analysis and alert validation system in accordance with some example embodiments of the present invention.

DETAILED DESCRIPTION

Example embodiments will now be described more fully hereinafter with reference to the accompanying drawings, in which some, but not all embodiments are shown. Indeed, the embodiments may take many different forms and should not be construed as limited to the embodiments set forth herein; rather, these embodiments are provided so that this disclosure will satisfy applicable legal requirements. Like reference numerals refer to like elements throughout. The terms "data," "content," "information," and similar terms may be used interchangeably, according to some example embodiments, to refer to data capable of being transmitted, received, operated on, and/or stored. Moreover, the term "exemplary", as may be used herein, is not provided to convey any qualitative assessment, but instead merely to convey an illustration of an example. Thus, use of any such terms should not be taken to limit the spirit and scope of embodiments of the present invention.

In some examples, engineers, technicians, nurses, and many other users in the modern world spend a great deal of time reacting to computer-generated alarms, alerts, and other indications, which result in a high false-positive rate. In some cases the false positive rate may be over 99%. One extreme example may be found with respect to airport baggage-screeners, where most screeners never see an actual event in their entire working career. Identifying rare events is a difficult thing for users to do well, because the human brain is not well-suited to dealing with this kind of situation. For example, if a user has only ever seen or generally only sees certain alarms as false-positives, the user may have a tendency to assume that all future alarms will also be false positives. Such cases occur, especially in instances in which operators deal with a large number of alarms, and, as such, may only have a few minutes for each individual alarm. In some examples, a level of validation of an alert along with corresponding alert validation text, which in some examples may include a situational analysis text, may provide not only an indication of the validity of an alert condition, but additional text that provides an explanation and the context in which the validity decision was made, as is described in some examples herein.

In order for a user, decision maker or the like to determine whether the alert validation decision was the correct decision, the user or decision maker may need to have an adequate awareness of the current condition or situation (e.g. situational awareness). Situational awareness may be defined as the perception of environmental elements with respect to time and/or space, the comprehension of their meaning, and the projection of their status after some variable has changed, such as time, or based on the happening of an event such as an alarm or alert. In other words, situational awareness is a state achieved when information that is qualitatively and quantitatively determined as suitable for particular purpose is made available to a user by engaging them in in an appropriate information exchange pattern or mental model. Situational awareness involves being aware of what is happening in the vicinity of a person or event to understand how information, events, and/or one's own actions may impact goals and objectives, both immediately and in the near future. Situational awareness may also be related to the perception of the environment critical to decision-makers in complex, dynamic areas from aviation, air traffic control, power plant operations, military command and control, engineering, machine monitoring, oil and gas, power plant monitoring, nuclear energy and emergency services such as firefighting and policing. Lacking or inadequate situational awareness has been identified as one of the primary factors in accidents attributed to human error.

Accurate mental models are one of the prerequisites for achieving situational awareness. A mental model can be described as a set of well-defined, highly-organized yet dynamic knowledge structures developed over time from experience. As such, in order to assist a user, such as a decision maker, in analyzing an alert validation decision, an alert validation text may be generated, as is described herein, that when combined with a user's mental model, may enable the user to achieve a level of situational awareness and/or understanding to enable that user to make a decision. For example, a doctor investigating a heart rate alarm may require an alert validation text pertaining to related data (e.g., blood pressure, respiration rate, or the like), actions which could affect heart rate (e.g., medication, surgery, or the like), and/or background information (e.g., genetics, medical conditions or the like). All of this information helps the doctor correctly interpret and ultimately validate the heart rate alarm alert validation text. In some cases, the doctor may need dynamic as well as static information; for example, dynamic information such as how has the patient's heart rate changed in the past when a drug was administered and static information such as historical data related to a patient's conditions. In some cases, without proper situational awareness a user will not trust or otherwise follow a recommendation provided by a user, a computer, a machine, a subordinate or the like.

Consequently, the example method, apparatus and computer program product described herein is configured to generate an alert validation text that enables a user to assess the validity of an alert condition. As is described herein, in some example embodiments, an alert condition may be accessed or otherwise received from an alert source, a monitoring system or by other alert detection methods. In response to the alert condition, the method, apparatus and computer product may select the data channel having the alert condition as the primary data channel. Further, one or more related data channels may be indicated as related based on the alert condition, a set of rules, a domain model or the like. Patterns located in the primary data channel and/or the one or more related data channels and the relationships between them may be used by the example method, apparatus and computer program product to determine whether the alert condition is a valid or invalid alert condition. In an instance in which the alert condition is determined to be valid, a text may be generated that describes the reasons why the alert was deemed to be valid as well as contextual information related to the alert condition. In some cases, a situational analysis text may be generated in an instance of a valid alert condition. In instances in which the alert condition is deemed to be invalid, an invalid alert text may be generated that includes, but is not limited to, the reasons why the alert was deemed to be invalid, as well as contextual information related to the alert condition. In some cases, a situational analysis text may also be generated in an instance of an invalid alert condition.

FIG. 1 is an example block diagram of example components of an example situational analysis and alert validation environment 100. In some example embodiments, the situational analysis and alert validation environment 100 comprises an alert reception system 102, a data analysis system 104, an alert validation system 106, a natural language generation system 108 and one or more data sources, such as but not limited to, one or more of raw input data 110, historical data 112, a domain model 114 and/or an event log 116. The alert reception system 102, the data analysis system 104, the alert validation system 106, and/or the natural language generation system 108 make take the form of, for example, a code module, a component, circuitry and/or the like. The components of the situational analysis and alert validation environment 100 are configured to provide various logic (e.g. code, instructions, functions, routines and/or the like) and/or services related to the generation of situational analysis texts and/or the validation of an alert condition. As is used herein, a situational analysis text may be combined with text indicating the validity of the alert condition, and as such would, in some examples, result in an alert validation text.

In some example embodiments an alert reception system 102 is configured to receive an indication of an alert condition (e.g. an alert received from a source such as, but not limited to, another system, a monitoring system or the like), a violation of a constraint (e.g. a data value over a threshold, within a threshold for a period of time and/or the like), a user input or the like. The alert reception system 102 may in some example embodiments be in data communication with an alert monitoring system, machine monitoring systems, alarm centers, sensors and/or the like. In examples in which the alert reception system 102 is in communication with a monitoring system, the alert reception system 102 may receive a report, that includes but is not limited to an identifier, an identification of a machine or sensor that is experiencing the alert, the type of alert, a description, a title, and dates for maintenance requests related to the alert and/or the date time group (e.g. a set of characters, usually in a prescribed format, which may express the year, the month, the day of the month, the hour of the day, the minute of the hour, and/or the time zone) for the alert. Other alert condition information may be received and/or otherwise accessed in an alert database via an alert monitoring system. However, in some example embodiments, the methods, apparatus and computer products described herein may operate without an alert reception system and/or the alert reception system 102 may be embodied by the data analysis system 104.

Alternatively or additionally, the alert reception system 102 may be further configured to determine whether the alert condition has been intermittently active in the period leading up to the notification time, such as the notification time in a most recent alert condition. In some examples, intermittent activity refers to an instance in which the alert has been cycling between on and off for a period of time. In some cases, an off condition with respect to the intermittent alarm condition may be related to a threshold, for example, the threshold may identify a period in which the alert must be off or not active for a new alert to be generated instead of an intermittent alarm condition being triggered. The threshold may be determined based on the domain model and/or may be indicated by a user as a global parameter. Alternatively or additionally, the alert reception system may determine whether an alert validation was performed for a current alert condition or for a past alert condition, such as by the alert validation system 106, and if so, the outcome of the alert validation.

Alternatively or additionally, the alert reception system 102 is further configured to gather information, such as via raw input data 110, historical data 112, event log 116 or the like, on the history of an alert condition over a particular time period; for example, how often has the alert condition been triggered, how long was the alert condition active, or how often was the alert validated or not validated. In some examples, the alert reception system 102 may further identify if a maintenance request is currently pending for an alert condition and, if so, a current status of the maintenance request. Closed or completed maintenance requests may also be determined by the alert reception system 102. A time period used to search for historical information about the alert condition may be predetermined, set by a user, set according to a domain model and/or the like. In some examples, the time period may be configured to exclude intermittent alert condition activity as described herein.

Alternatively or additionally, the alert reception system 102 may further be configured to determine if there are other active alerts and maintenance requests on the unit or machine that triggered the alarm. For example, a single machine may monitor heart rate, blood pressure, etc. and as such the alert reception system 102 may be configured to check each sensor on a particular machine, in this case a human body. Alternatively, a machine may have a plurality of sensors that monitor temperature, pressure, vibrations or the like of various components of a machine and, as such, the alert reception system may be configured to check each one of the sensors for active alerts. The machine or unit definition (e.g. components that belong to the machine or unit) may be defined by a user, the domain model or the like. In other example embodiments, the alert reception system may also check if there are active alert conditions of the same alert type on other components, units or machines. The alert reception system 102 may further check if there are open maintenance requests on the components, machines or the like.

Alternatively or additionally, the alert reception system 102 may further gather or otherwise access information and/or data that refers to the status of a machine or unit having the alert condition. The information and/or data includes but is not limited to the functionality of the machine or unit, the most recent start or stop times, maintenance times and/or the like. For example, the alert reception system 102 may determine whether a machine or unit has been started or stopped in the last 24 hours.

In some example embodiments, the data analysis system may comprise a data analyzer 120 and/or a data interpreter 122. The data analyzer 120 is configured to input raw data, such as the raw data contained in the raw input data 110, historical data, such as the historical data contain in the historical data 112 and/or other data determined or otherwise obtained by the alert reception system 102 or the data analysis system 104. The receipt or input of the raw input data and/or historical data may occur in response to an alert condition, such as is indicated by or otherwise received via the alert reception system 102. Alternatively or additionally the data analyzer 120 may be configured to receive or input raw input data continuously or semi-continuously, such as via a data stream, and determine an importance of the raw input data (e.g., whether the data violates a constraint, satisfies a threshold and/or the like) in order to detect or otherwise determine the presence of an alert condition. In other words, in some example embodiments, the data analysis system 104, the data analyzer 120 and/or the data interpreter 122 may function as or otherwise embody the alert reception system 102 and/or an alert detection system.

Raw input data may include data such as, but not limited to, time series data that captures variations across time (e.g. profits, rainfall amounts, temperature or the like), spatial data that indicates variation across location (e.g. rainfall in different regions), or spatial-temporal data that combines both time series data and spatial data (e.g. rainfall across time in different geographical output areas). The raw input data contained or otherwise made accessible by the raw input data 110 may be provided in the form of numeric values for specific parameters across time and space, but the raw input data may also contain alphanumeric symbols, such as the RDF notation used in the semantic web, or as the content of database fields. The raw input data 110 may be received from a plurality of sources and, as such, data received from each source, sub source or data that is otherwise related may be grouped into or otherwise referred to as a data channel.

In some example embodiments, the data analyzer 120 is further configured to input historical data, such as from historical data 112. Similar to the raw input data 110, historical data, stored on or otherwise made accessible via historical data 112, may be provided in the form of numeric values for specific parameters across time and space. The historical data may also contain alphanumeric symbols, such as the RDF notation used in the semantic web, or as the content of database fields. The raw input data 110 may be received from a plurality of sources and, as such, data received from each source, sub source or data that is otherwise related may be grouped into or otherwise to referred to as a historical data channel. A historical data channel may include historical information relating to the current alert condition, data in the primary data channel, the one or more related data channels and/or the like. In some cases, the historical data 112 may be related to the machine apparatus, sensor, device, tool, situation or the like that caused or is otherwise related to the alert condition. Alternatively or additionally, the historical data 112 may include additional historical data such as past events, previous alert conditions, contextual information about sensors, machines and/or the like.

In some example embodiments, the data analyzer 120 is configured to detect patterns and trends in the one or more data channels that are derived from the raw input data and/or the historical data to provide a set of abstractions. For example, a time-series dataset may contain tens of thousands of individual records describing the temperature at various time points on a component piece of machinery over the course of a day with a sample once every two or three seconds. Trend analysis may then be used to identify that the temperature changes in a characteristic way throughout certain parts of the day. As such, the trend analysis is configured to abstract those changes over time into an abstraction that is representative of the change over time.

In some example embodiments, the data analyzer 120 may be configured to fit a piecewise linear model to the data received in the primary data channel, related data channel or the like. The fitting of the piecewise linear model may include filtering in some examples. For each trend in the raw input data, the data analyzer 120 may determine a start and/or end time values, qualitative direction (e.g. up, down, steady), qualitative stability (e.g. stable, unstable), threshold status (e.g. normal, high, low, unknown at start, end of trend and/or the like). The data analyzer 120 may be configured to perform the fitting of the piecewise linear model for one or more time scales; for example, over a short term (e.g. 6 hours) using the time of the alert condition to determine how the machine or unit was acting at the time the alert became active. A longer time period (e.g. 2 months) may also be analyzed. In some examples, the longer time period may ignore equipment off periods and/or the like.

In some example embodiments, the data analyzer 120 is further configured to determine a first or primary data channel. In some examples, a first or primary data channel may be selected based on a selection by a user, via a user interface, may be selected based on the happening of a condition such as, but not limited to, an alert, an alarm, an anomaly, a violation of a constraint, a warning, may be predetermined and/or the like. In some cases, the primary data channel is generally related to, for example, the raw input data and/or data channel that caused the alert condition. In some example embodiments, the data analyzer 120 may also be configured to identify data channels (e.g. secondary or related channels) that are related to the primary data channel. Alternatively or additionally, relations between data channels may be defined by the domain model 114 and therefore accessible by the data analyzer 120.

In some example embodiments, a secondary or related data channel is selected by the data analyzer 120. In other example cases, a plurality of secondary or related data channels may be selected by the data analyzer 120. The one or more secondary or related data channels may be selected based on the detection of important, anomalous, unexpected or otherwise flagged behavior in the second or related channel. In some examples, the second or related channel is compared to one or more patterns detected in the primary data channel over a similar or related time period. For example, a first data channel may indicate a rise in heart rate, whereas a second data channel may indicate a stable or even a decline in respiration rate. Generally, a medical professional may expect a respiration rate to rise along with heart rate, and, as such, a stable respiration rate when heart rate is rising is generally unexpected. In some examples, unexpected behavior may lead to a life threatening condition, be indicative of a dangerous condition, or the like. Alternatively or additionally, a plurality of related channels may also be considered, for example, oxygen levels, blood pressure and/or the like.

Relationships between data channels may be defined as important or unexpected or may represent anomalous behavior as defined by a qualitative model such as the domain model 114. In some examples, the domain model 114 is a representation of information about a particular domain. For example, a domain model may contain an ontology that specifies the kinds of objects, concepts and/or the like that may exist in the domain in concrete or abstract form, properties that may be predicated of the objects, concepts and the like, relationships that may hold between the objects concepts and the like, and representations of any specific knowledge that is required to function in the particular domain. In some cases, the domain model 114 represents the mental model used for situational awareness in a particular domain. In some examples, multiple domain models may be provided for a single domain. For example, domains may include, but are not limited to, medical, oil and gas, logistics, news and reporting, industrial, power, weather, legal, financial, nuclear and/or the like.

In some examples, relationships may be defined with respect to one or more sensors, sensor types, monitoring equipment or the like. For example, an alert on a first sensor may have a relationship with another sensor on the same machine or on other related machines. The relationship may further include an indication that the related sensor generally detects movement in the same direction as the primary sensor or that the related sensor generally moves in an opposite direction from the primary sensor. An importance level may be also be assigned to a particular sensor, such as by a user, the domain model or the like. In some examples, this importance level may be used to determine an importance of a particular sensor event. In some cases, one or more sensors may be indicated as always to be included in a text.

Figure 6:
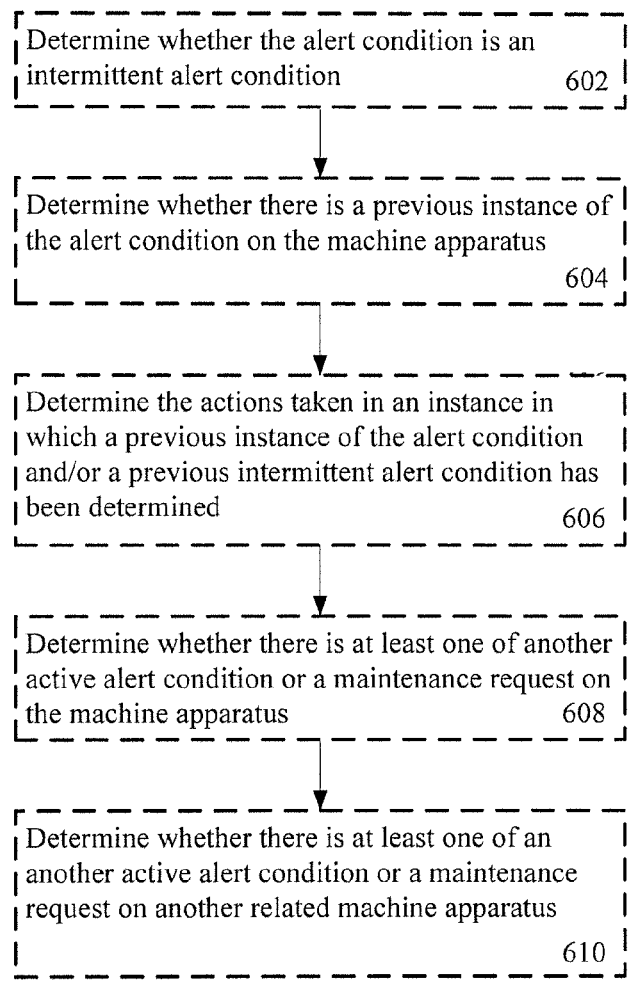

Alternatively or additionally, a diagnostic model may be configured to determine or otherwise identify one or more possible causes of an alert condition; see e.g. FIG. 6. Based on the one or more possible causes of the alert condition, the diagnostic model may be further configured to determine which of the one or more data channels should be examined to verify and/or disprove the one or more possible causes. These data channels may be related data channels. For example, the diagnosis model may identify allergic reaction to medication as one reason for a spike in heart rate. It may also determine that if allergic reaction is suspected, a respiration rate data channel should be examined to verify and/or disprove this diagnosis, because respiration rate would become erratic if the underlying cause was allergic reaction. As such, in this example, respiration rate may be identified as a related data channel.

Alternatively or additionally, the method, apparatus and computer program product described herein may further provide and/or otherwise access a rule language that is configured to qualitatively specify expected relationships between data channels (e.g. a primary data channel and one or more related data channels). The rule language may further be configured to specify or otherwise indicate instances in which related data channels, related events and/or the like are mentioned in a situation analysis text. In some examples, the rules may be built via a user interface, using the rule language that may extract or otherwise receive information related to the data channels and the relationships between them. In some cases the data channels and/or relationships may be discovered by analyzing one or more data sources. The rule language may further provide information related to the context of one or more data channels and alerts that may be generated or accessed based on those data channels, for example equipment status, alert history, and status of similar equipment elsewhere.

The data analyzer 120 may then identify trends, spikes, steps or other patterns in the data channels to generate abstractions that summarize the patterns determined in the primary data channel and/or the other related data channels. Alternatively or additionally, the data analyzer 120 may also be configured to perform pattern detection on the raw input data irrespective of data channels or the receipt of an alarm condition.

In some example embodiments, a contextual channel may also be selected by the alert reception system 102, the data analysis system 104, the data analyzer 120 or the like. A contextual channel is a data channel that provides a background or circumstance that led to or otherwise influenced the one or more key events and/or the one or more significant events (e.g. a patient is 43 years old and male, or information on a type of sensor that detected the alert condition). For example, a contextual channel may indicate an event, such as a medical treatment that was applied at the time of or just prior to the rise of the heartbeat and the fall or steady state of the respiration rate. Alternatively or additionally a plurality of data channels may also be included based on an anomaly or unexpected behavior. In some examples, one or more data channels may be selected even though the one or more data channels are representative of expected behavior. For example, in the medical domain, a medical professional may expect to see a description of both heart rate and respiration rate in a text even if both are behaving in expected ways, since expected behavior may be indicative of an important result, namely a clean bill of health.

In yet further example embodiments, events may also be determined by the alert reception system 102, the data analysis system 104, the data analyzer 120 or the like. For example, in the medical profession, an event may be the application or injection of some medication, whereas in the machinery domain an event may be the startup of a particular machine. An event may be described in a contextual channel, may be entered into an event log, such as event log 116 (e.g. an explicit listing of events), that is input with the raw input data, may be detected within a data channel (e.g. application of a medication received via an IV line data channel) and/or may be inferred based on the raw input data (e.g. alert occurred shortly after startup).

Alternatively or additionally, the data analysis system 104, the data analyzer 120 or the like may be configured to determine one or more problems or inconsistencies with the raw input data, historical data or other data input in the data analysis system 104. In some cases, the data problems may be in the raw input data, however in other cases the data problems may be a result of a communications error. In some examples, the data analyzer 120 may detect missing data in an instance in which data was not received over a predetermined duration (e.g. exceeds the time in which values are reported). In other examples, a sensor's values may not have changed over a predetermined period before an alert condition was indicated; such a case may indicate a frozen data condition. Frozen data may be identified in an instance in which a machine or unit is determined to be running during a period (e.g. based on a determined equipment status), the sensors are float valued and/or the sensor is not excluded from the frozen check. In other examples, raw input data may be checked to determine if the values fall outside those physically possible (e.g. temperatures that would cause melting). Other verification may include error tokens, inconsistent values and/or the like.

A data interpreter, such as data interpreter 122, may then be configured to input the abstractions and generate one or more messages based on a determined importance level and/or relationships between the abstractions identified in the one or more data channels (e.g. primary data channel, one or more related data channels, historical data channels and/or the like). The one or more messages may be generated based on a domain model, a requirements analysis, a corpus analysis and or the like. The one or more messages may then be populated or otherwise instantiated based on data or information in the primary data channel, the one or more related data channels, the historical data, the contextual channel, one or more events and/or the like.

In some examples, messages are language independent data structures that correspond to informational elements in a text and/or collect together underling data in such a way that the underlying data can be linguistically expressed. In some examples, messages are created based on a requirements analysis as to what is to be communicated for a particular scenario (e.g. for a particular domain). A message typically corresponds to a fact about the underlying data (for example, the existence of some observed event) that could be expressed via a simple sentence (although it may ultimately be realized by some other linguistic means). For example, to linguistically describe wind, a user may want to know a speed, a direction, a time period or the like, but also the user wants to know changes in speed over time, warm or cold fronts, geographic areas and or the like. In some cases, users may not even want to know wind speed, but simply want to be told of dangerous or otherwise interesting wind conditions. Thus, a message related to wind speed may include fields to be populated by data related to the speed, direction, time period or the like, and may have other fields related to different time points, front information or the like. The mere fact that wind exists may be found in the data, but to linguistically describe "light wind" or "gusts" different data interpretation must be undertaken as is described herein.

In some examples, a message is created by the data interpreter 122 in an instance in which the raw input data or the historical data warrants the construction of such a message. For example, a wind message would only be constructed in an instance in which wind data was present in the raw input data. Alternatively or additionally, while messages may correspond directly to observations taken from the raw data input, others, however, may be derived from the observations by means of a process of inference. For example, the presence of rain may be indicative of other conditions, such as the potential for snow at some temperatures. Alternatively or additionally, in some example embodiments, the natural language generation system 108 may embody all or portions of the data analysis system 104, the data analyzer 120, and/or the data interpreter 122. In some example embodiments, the natural language generation system 108 may be configured to instantiate messages.

The concepts and relationships that make up messages may be drawn by the data interpreter 122 from an ontology (e.g. a domain model) that formally represents knowledge about the application scenario. For example, message structures may be defined by the domain model 114 based on a particular alert condition and/or the raw input data, such as but not limited to the primary and/or related data channels. Messages may also be derived from another data structure, may be user defined and/or the like. Each type of message may also be represented by a message template, which expresses a relationship between instances of a number of concepts; the message template contains slots which may be filled in, or instantiated, using particular values that are derived from the raw input data.

As such, the data interpreter 122 is configured to instantiate a plurality of messages based on the raw input data derived from the key events, the significant events, the primary data channel, the one or more related data channels, the historical data, the events, the contextual channel and/or the like. In order to determine the one or more messages, the importance level of each of the messages and relationships between the messages, the data interpreter 122 may be configured to access the domain model 114 directly or indirectly via the data analyzer 120 or the like. The domain model 114 may contain information related to a particular domain or industry. In some examples, the domain model 114 may provide importance levels, single data channel limits related to normal behaviors in a domain (e.g. normal ranges), information related to anomalous behaviors and/or the like. In other examples, the domain model 114 may describe relationships between various events and/or phenomena in multiple data channels. For example in a weather domain, a domain model may indicate or otherwise instantiate an extreme weather message in an instance in which wind speeds that are related to hurricane type events or temperatures that may cause harm to humans or other animals or may cause damage or interference to shipping are present in the data. The extreme weather message may then be labeled as important, whereas typical temperatures or a typical wind message may not be marked as important in some examples. Alternatively or additionally, the domain model 114 may be configured to contain or otherwise have access to the diagnostic model.

In some example embodiments, the data interpreter 122 may be configured to annotate messages with an indication of their relative importance; this information can be used in subsequent processing steps or by the natural language generation system 108 to make decisions about which information should be conveyed and which information may be suppressed, such as by using the domain model 114. The data interpreter 122 may assign an importance level to the one or more messages based on the pattern itself (e.g. magnitude, duration, rate of change or the like), defined constraints (e.g. defined thresholds, constraints or tolerances), temporal relationships between the pattern in the primary data channel and patterns in other related data channels and/or the like. For example, a heart rate over 170 beats per minute, or 100 mile per hour winds, may be assigned a high level of importance. In some examples, messages that describe other patterns and/or constraints may be defined by the domain model 114. Alternatively or additionally, the data interpreter 122 may also be configured to annotate messages with information about how they are related to each other; for example, the data interpreter 122 might indicate that an event described in one message is assumed to have been caused by the event described in another message.

Using the importance level, the data interpreter 122 may assign certain ones of the messages that describe or are otherwise are instantiated with patterns or other data in the primary data channel as including key events. A key event may be selected or otherwise identified based on a predetermined importance level threshold, such as a threshold defined by a user, a constraint defined by the domain model 114, or the like. Alternatively or additionally, key events may be selected or otherwise identified based on those patterns in the primary data channel with the highest level of importance, those patterns that exceed or otherwise satisfy the pre-determined importance level threshold and/or the like. For example, a domain model or user preference may indicate that any messages having wind readings over 50 miles per hour may be designated as key events, whereas in other examples only a message with highest wind reading over a defined time period may be a determined to include a key event. In further examples, the importance level determination may be performed over a plurality of time scales that may be user defined, defined by the domain model or the like (e.g., one hour, one day, one week, one month and/or the like).

In some example embodiments, the data interpreter 122 may also be configured to determine the importance of messages that describe patterns or events detected in one or more secondary or related data channels. In some examples, the data interpreter 122 may determine one or more messages that describe patterns or events in the related data channels that overlap time-wise or occur within the same time period as the patterns in the primary data channel. For example, during the same time period as rain is detected, another data channel may detect temperature falling below the freezing point. The data interpreter 122 may then mark the one or more messages that describe patterns or events in the related channels as important, expected, unexpected or as having or not having some other property based on the domain model 114. For example, the domain model may suggest that the one or more patterns in the related data channel were expected to rise as they did in the primary channel. By way of example, as winds are rising, a wave height may then be expected to rise. In other cases, the behavior of the one or more related channels may be unexpected or may be anomalous when compared to the behavior of the primary data channel.

The one or more messages may be marked as including significant events based on the importance level, domain model 114, constraints, user settings or the like. For example, messages that include patterns or events in the related data channel that have an importance level above a predetermined threshold defined by the domain model 114, a user or the like, and may be marked as including significant events. In some example embodiments, messages including unexpected patterns or messages may also be categorized as significant events as they are suggestive of a particular condition or fault. Other messages including patterns or events may be determined to be significant events based on one or more constraints on channel value (e.g. expected range of values or the like), data anomalies, patterns marked as neither expected or unexpected that satisfy an importance level, and/or the like.

In some example embodiments, the data interpreter 122 may also be configured to determine the importance of messages built or otherwise instantiated using historical data, such as historical data 112, background information, event data, and/or the like. For example, historical data may contain information related to a previous alert condition and the actions taken or a result. Historical data may also provide indicators of the validity of an alert and/or provide additional information that may provide additional situational awareness.

In further example embodiments, the data interpreter 122 may be configured to generate one or more messages based on determined or otherwise inferred events from the one or more data channels, historical data, event data and/or the like. Events may include specific activities that may influence the one or more key events and/or may have caused the one or more significant events. In some examples, the one or more events may be inferred based in context with the one or more patterns in the primary and/or related data channels.

Alternatively or additionally events may be provided as a separate channel, such as a contextual channel, in the raw input data 110, the event log 116 or may be provided directly to the data interpreter 122. Alternatively or additionally, one or more messages may be generated based on the contextual channel.

In some examples, the data analysis system 104, the data analyzer 120 or the like may receive raw input data, such as the data in the following table, that illustrates a primary data channel (e.g. heart rate) and a related data channel (e.g. respiration rate):

| Time | Heart Rate | Respiration Rate |
|------|------------|------------------|
| 1    | 68         | 14               |
| 2    | 72         | 15               |
| 3    | 70         | 14               |
| 4    | 70         | 14               |
| 5    | 69         | 16               |
| 6    | 72         | 15               |
| 7    | 73         | 16               |
| 8    | 68         | 13               |
| 9    | 70         | 14               |
| 10   | 71         | 15               |
| 11   | 90         | 14               |
| 12   | 110        | 14               |
| 13   | 118        | 14               |
| 14   | 116        | 15               |
| 15   | 105        | 15               |
| 16   | 92         | 14               |
| 17   | 86         | 13               |
| 18   | 80         | 14               |
| 19   | 75         | 14               |
| 20   | 72         | 15               |
| 21   | 70         | 14               |
| 22   | 71         | 13               |
| 23   | 69         | 13               |
| 24   | 71         | 14               |

As is demonstrated by the raw input data in the table above, heart rate went above 115 beats per minute (bpm) at time point 13, thus causing an alert condition. As such, the alert reception system 102, the data analysis system 104 and/or the like may receive an indication of an alarm condition, such as by a patient monitoring system, patient monitoring equipment and/or based on the determination by the data analysis system 104 that the data indicates an alert situation. In response to the alert condition, the data analyzer 120 may cause the heart rate data channel to be the primary data channel. In other embodiments, a user, the domain model or the like may indicate that the primary data channel is the heart rate data channel. In some example embodiments, the data analyzer 120 may abstract or otherwise identify the rapid change of heart rate between time point 10 and time point 11 lasting to time point 15 for use by the data interpreter 122.

The data analyzer 120 may also determine whether a secondary or related data channel (e.g. respiration rate) has a pattern (e.g. no change when a change is generally expected) in a corresponding time period. In some examples, the corresponding time period may be the same time period or may be a later time period when compared to the time period of the key events. Further, the corresponding time period may, in some examples, be defined by a domain model, such as domain model 114. In some example embodiments, the data analyzer 120 may abstract or otherwise identify the relatively flat and/or steady respiration rate between time point 10 and time point 15 for use by the data interpreter 122.

In some example embodiments, the data interpreter 122 is configured to generate one or more messages based on the raw input data in the one or more data channels. As described herein, messages are language independent data structures that correspond to informational elements in a text and/or collect together underlying data in such a way that the underlying data can be linguistically expressed. Using the heart rate example, a message may include portions of the raw input data, to include abstractions of the data, but may also include additional distinctions necessary for the generation of text as the raw input data is likely to be insufficient for such a purpose. For example, a HeartRateSpike message may be instantiated using the raw input data and such a message may include: a time and relative variation in terms of heart rate change or peak heart rate, a time period and a direction. In some examples, another message may be generated on related channels, historic data, events and/or the like. In some examples, the HeartRateSpike message may be related to an Alert Message that contains information relating to the alert itself. For example, in an instance in which caffeine was applied prior to the heart rate spike, a message may be generated to identify such an event. Such a message may be an Event message that is instantiated with an event time and an event description, such as from the event log 116; for example, a message that indicates that caffeine had been orally administered prior to the spike in heart rate. Other messages such as RespirationRate (e.g. respiration rate stable=yes), HeartRateAlertHistorical (e.g. previous alert condition quantity=2, time=yesterday), HeartRateHistorical (e.g. heart rate trend=no change, time period=10 days) may be instantiated to include information about the related data channels and/or historical data. Alternatively or additionally, the natural language generation system 108, the document planner 130 and/or the like may be configured to generate the one or more messages.

In some example embodiments, an alert validation system 106 is configured to determine the validity of a current alert condition based on the one or more messages received from the data analysis system 104, the raw input data 110, the historical data 112 and/or the domain model 114. In some example embodiments, alert validation may be determined based on the length an alert has been intermittently on, in an instance the alert is intermittent; open maintenance requests based on the alert; other alarms on the same machine or unit; active alert conditions on other units; duration of the alert condition; sensor providing input data that is trending up/down/steady; detection of unexpected behavior; data errors and/or the like.

In some examples, the alert validation system 106 may use machine learning to determine the validity of an alert (e.g. building a decision tree based on a domain model and historical alert validation data). As such, using for example a decision tree, the alert validation system 106 may be configured to determine the validity of the alert condition. In other examples, an alert may be determined to be invalid by the alert validation system in an instance in which there are data problems with a sensor or the machine that the sensor is monitoring is off or other otherwise not functioning. In an instance in which a current maintenance request is identified, the current alert condition may be merged with said current maintenance request.

In some example embodiments, the alert validation system may generate additional messages for use by the natural language generation system 108 in generating an alert validation text. As such, these messages may include data relating to contextual information, such as, the key events, significant events, historical data and/or the like. For example, context information may include data that would enable a decision maker to make a decision or understand a current situation, information to be used by a mental model (e.g. satisfy a user's internal list of items to check when validating an alert), information that enables a user to override a decision and/or the like. One such message may provide an indication to ignore the alarm, because the change in heart rate was probably caused by the caffeine.

In some example embodiments, a natural language generation system, such as natural language generation system 108, is configured to generate phrases, sentences, text or the like which may take the form of natural language text. The natural language generation system 108 comprises a document planner 130, a microplanner 132 and/or a realizer 134. Other natural language generation systems may be used in some example embodiments, such as a natural language generation system as described in Building Natural Language Generation Systems by Ehud Reiter and Robert Dale, Cambridge University Press (2000), which is incorporated by reference in its entirety herein.

The document planner 130 is configured to input the one or more messages that are generated and/or instantiated by the data analysis system 104. The document planner 130 is further configured to determine how to arrange those messages to describe the patterns in the one or more data channels derived from the raw input data. The document planner 130 may comprise a content determination process that is configured to select the messages, such as the messages that describe the key events and/or the significant events, that are be included in a situational analysis text and/or an alert validation text.

The document planner 130 may also comprise a structuring process that determines the order of messages referring to the key events and/or significant events to be included in a natural language text. In some example embodiments, the document planner 130 may access one or more text schemas for the purposes of content determination and document structuring. A text schema is a rule set that defines the order in which a number of messages are to be presented in a document. For example, an event message (e.g. medication injection) may be described prior to a key event message (e.g. rise in heart rate). In other examples, a significant event message (e.g. falling respiration rate) may be described after, but in relation to, a key event message (e.g. rise in heart rate). By way of further example a document plan may include, but is not limited to, an AlertMessage, a HeartRateSpike message and then a Respiration Rate message. An Event message, HeartRateAlertHistorical message and HeartRateHistorical message may then follow in the example document plan.

The output of the document planner 130 may be a tree-structured object or other data structure that is referred to as a document plan. In an instance in which a tree-structured object is chosen for the document plan, the leaf nodes of the tree may contain the messages, and the intermediate nodes of the tree structure object may be configured to indicate how the subordinate nodes are related (e.g. elaboration, consequence, contrast and/or the like) to each other.

In some example embodiments, the document planner 130 may be configured for generation of alert validation texts. As such, the document planner 130 may include an example paragraph containing one or more of an alert information message (e.g. alert name, unit, time), an intermittent alert message in an instance in which an alert has been on intermittently (e.g. start time), and/or an intermittent validation summary message in an instance in which the alert has been on intermittently and alert validation has been completed, such as by the data analysis system 104 (e.g. number of times validated, number of times not validated).

In further examples, the document planner 130 may also be configured to generate an example paragraph relating to the behavior of the sensor via the raw input data. This paragraph may include but is not limited to messages related to data problems if there are data problems, messages related to primary trends in the form of key events and/or a machine status message (e.g. on/off, on duration, multiple starts or the like). In an instance in which the document planner 130 is configured to provide a recommendation, one or more recommendation messages and/or explanations may be included by the document planner 130.

Alternatively or additionally, the document planner 130 may further include one or more of a concurrent alerts summary, in an instance in which there are similar alerts on related units; a similar alert summary; active maintenance request messages in an instance in which there are active maintenance requests for this alert condition on the machine (e.g. number, status) and related maintenance request messages in an instance in which there are active maintenance requests for this alert condition on related units; a data problems message and/or previous history messages.

A sample document plan may include, but is not limited to, document plan 250 of FIG. 2b. Document plan 250 may include but is not limited to one or more messages, such as message 252.

The microplanner 132 is configured to modify the document plan from the document planner 130, such that the document plan may be expressed in natural language. In some example embodiments, the microplanner 132 may perform aggregation, lexicalization and referring expression generation. In some examples, aggregation includes, but is not limited to, determining whether two or more messages can be combined together linguistically to produce a more complex sentence. For example, one or more key events may be aggregated so that both of the key events can be described by a single sentence. For example the alert information message and the HeartRateSpike message may be combined using the term because.

In some examples, lexicalization includes, but is not limited to, choosing particular words for the expression of concepts and relations. For example, the phrase 'sounded an alarm" may be used to describe an alert condition or "administered" may be used to describe the causal event. Other descriptive phrases such as "respiration rate" may be determined to describe one or more related channels.

In some examples, referring expression generation includes, but is not limited to, choosing how to refer to an entity so that it can be unambiguously identified by the reader. For example, in a first sentence "John Smith" and a heart rate alarm may be used where "he" or "it" may be used in subsequent sentences.

The output of the microplanner 132, in some example embodiments, is a tree-structured text specification whose leaf-nodes are phrase specifications, and whose internal nodes express rhetorical relations between the leaf nodes. A tree-structured text specification may include, but is not limited to, text specification 260 of FIG. 2b, having one or more phrase specifications, such as phrase specification 262. A phrase specification may correspond to a sentence or a sub-sentence fragment (e.g. a title) and are produced from one or more messages. A phrase specification is configured to contain one or more syntactic constituents (e.g. subject, verb, prepositional phrase and/or the like) and one or more syntactic features (e.g. tense).

A realizer 134 is configured to traverse the tree-structured text specification to express the tree-structured text specification in natural language. The realization process that is applied to each phrase specification in a text specification makes use of a grammar which specifies the valid syntactic structures in the language and further provides a way of mapping from phrase specifications into the corresponding natural language sentences. The output of the process is, in some example embodiments, a well-formed natural language text. In some examples, the natural language text may include embedded mark-up. The output of the realizer 134, in some example embodiments, is the alert validation text. The realizer may also output situational analysis text or a narrative that is configured to describe or otherwise summarize the one or more key events, the one or more significant events, the one or more contextual channels, and/or the one or more events.

By way of example, the realizer may output the following alert validation text in response to the text specification shown above:

John Smith's heart rate monitor sounded an alarm at 10.56 because his heart rate went above 115 beats per minute (bpm). His respiratory rate and oxygen saturation did not change. Caffeine, which can affect heart rate, had been orally administered to John at 10.54. This alarm had gone off twice yesterday, but in both cases heart rate quickly reverted to 70 bpm. John's heart rate has not shown any long-term upward or downward trends since he was admitted 10 days ago.

Recommendation: Ignore alarm, because the change in heart rate was probably caused by the caffeine.

Alternatively or additionally, the natural language generation system 108 may be configured to generate a graph to display one or more key events that are detected in a data channel. In some example embodiments, the graph may also include one or more significant events in one or more related channels and/or events. In further examples, a time period or duration of the data shown in the graph may be selected such that the displayed graph illustrates the portion of the data channel that contains the one or more key events. The output graph is further configured to include textual annotations that provide a textual comment, phrase or otherwise is configured to explain, using text, the one or more key events, the one or more significant events and/or the events in a contextual channel in natural language. In further examples, the textual annotations are generated from the raw input data and further are designed, in some examples, to textually describe identified patterns, anomalies and/or the context of the graph. In some examples, a narrative (e.g. situational analysis text) may be included with the graph that provides situational awareness or an overview of the data/patterns displayed on and/or off of the graph.

FIG. 2a illustrates an example alert monitoring system in an example machine monitoring domain according to some example embodiments described herein. FIG. 2a illustrates a first machine 202 and a second machine 204. The first machine may comprise component 210 having a sensor 220 and component 212 having a sensor 222. The second machine may comprise component 214 having a sensor 224 and component 216 having a sensor 226.

As is described herein, the machines 202 and 204, the components 210-216 and/or the sensors 220-226 may be defined in terms of relationships. For example sensor 220 may be related to sensor 222 with a relationship defined as the data generated by sensor 220 moves in the opposite direction of sensor 222 (e.g. 220 is falling and 222 is rising). Other relationships, such as a relation between sensor 220 and 224, may also be defined in some example embodiments. Each of the relationships may be given an importance and/or otherwise may be weighted based on the importance level of the relationship between the sensors, such as 220 and 222, components 210 and 212 and/or the like. Relationship and importance may be determined for each machine, component, sub component, sensor and/or the like. Metadata and/or an ontology may also be specified that includes a linguistic description or title for each component, sub component or the like.

By way of example, the data analysis system 104 may perform one or more of the following in an instance in which an alarm condition is detected with respect to sensor 220. In some examples, the data analysis system may determine whether the alert condition is an intermittent alert condition, by determining the last active alert for sensor 220. In further examples, the data analysis system 104 may determine the alert history and/or maintenance history for the sensor 220, the component 210 and the machine 202. Such historical information may be used to validate the alert condition and/or for the purposes of generating a situational analysis text. Current event information may be determined for the machine 202 and/or the components 210 and 212 that includes but is not limited to current status, last startup time and/or the like.

The data analysis system 104 may then check for active alerts and/or maintenance requests on the same equipment, such as with respect to sensor 222, component 212 and/or machine 202. The data analysis system 104 may also check for active alerts and/or maintenance requests on a related machine, such as machine 204, and/or related components, such as components 214 and 216. The data analysis system 104 may then analyze the data received via sensors 220-226 as is described with respect to FIG. 1.

FIG. 3 is an example block diagram of an example computing device for practicing embodiments of an example situational analysis and alert validation system. In particular, FIG. 3 shows a computing system 300 that may be utilized to implement a situational analysis and alert validation environment 100 having an alert reception system 102; a data analysis system 104 including, in some examples, a data analyzer 120 and a data interpreter 122; an alert validation system 106; a natural language generation system 108 including, in some examples, a document planner 130, a microplanner 132 and/or a realizer 124; and/or an optional user interface (not shown). One or more general purpose or special purpose computing systems/devices may be used to implement the alert reception system 102, the data analysis system 104, the alert validation system 106 and/or the natural language generation system 108. In addition, the computing system 300 may comprise one or more distinct computing systems/devices and may span distributed locations. In some example embodiments, the alert reception system 102, the data analysis system 104, the alert validation system 106 and/or the natural language generation system 108 may be configured to operate remotely via the network 350. In some example embodiments, a pre-processing module or other module that requires heavy computational load may be configured to perform that computational load and thus may be on a remote device or server. For example, the data analysis system 104 may be accessed remotely. Furthermore, each block shown may represent one or more such blocks as appropriate to a specific example embodiment. In some cases one or more of the blocks may be combined with other blocks. Also, the alert reception system 102, the data analysis system 104, the alert validation system 106 and/or the natural language generation system 108 may be implemented in software, hardware, firmware, or in some combination to achieve the capabilities described herein.

In the example embodiment shown, computing system 300 comprises a computer memory ("memory") 301, a display 302, one or more processors 303, input/output devices 304 (e.g., keyboard, mouse, CRT or LCD display, touch screen, gesture sensing device and/or the like), other computer-readable media 305, and communications interface 306. The processor 303 may, for example, be embodied as various means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an application-specific integrated circuit (ASIC) or field-programmable gate array (FPGA), or some combination thereof. Accordingly, although illustrated in FIG. 3 as a single processor, in some embodiments the processor 303 comprises a plurality of processors. The plurality of processors may be in operative communication with each other and may be collectively configured to perform one or more functionalities of the situational analysis and/or alert validation system as described herein.

The alert reception system 102, the data analysis system 104, the alert validation system 106 and/or the natural language generation system 108 are shown residing in memory 301. The memory 301 may comprise, for example, transitory and/or non-transitory memory, such as volatile memory, non-volatile memory, or some combination thereof. Although illustrated in FIG. 3 as a single memory, the memory 301 may comprise a plurality of memories. The plurality of memories may be embodied on a single computing device or may be distributed across a plurality of computing devices collectively configured to function as the situational analysis texts and/or alert validation system. In various example embodiments, the memory 301 may comprise, for example, a hard disk, random access memory, cache memory, flash memory, a compact disc read only memory (CD-ROM), digital versatile disc read only memory (DVD-ROM), an optical disc, circuitry configured to store information, or some combination thereof.

In other embodiments, some portion of the contents, some or all of the components of the alert reception system 102, the data analysis system 104, the alert validation system 106 and/or the natural language generation system 108 may be stored on and/or transmitted over the other computer-readable media 305. The components of the alert reception system 102, the data analysis system 104, the alert validation system 106 and/or the natural language generation system 108 preferably execute on one or more processors 303 and are configured to generate situational analysis texts and/or perform alert validation, as described herein.

Alternatively or additionally, other code or programs 330 (e.g., an administrative interface, a Web server, and the like) and potentially other data repositories, such as data repository 340, also reside in the memory 301, and preferably execute on one or more processors 303. Of note, one or more of the components in FIG. 3 may not be present in any specific implementation. For example, some embodiments may not provide other computer readable media 305 or a display 302.

The alert reception system 102, the data analysis system 104, the alert validation system 106 and/or the natural language generation system 108 are further configured to provide functions such as those described with reference to FIG. 1, the alert reception system 102, the data analysis system 104, the alert validation system 106 and/or the natural language generation system 108 may interact with the network 350, via the communications interface 306, with remote data sources/alert systems 356 (e.g. remote reference data, remote performance data, remote aggregation data, remote alert systems and/or the like), third-party content providers 354 and/or client devices 358. The network 350 may be any combination of media (e.g., twisted pair, coaxial, fiber optic, radio frequency), hardware (e.g., routers, switches, repeaters, transceivers), and protocols (e.g., TCP/IP, UDP, Ethernet, Wi-Fi, WiMAX, Bluetooth) that facilitate communication between remotely situated humans and/or devices. In some instance the network 350 may take the form of the internet or may be embodied by a cellular network such as an LTE based network. In this regard, the communications interface 306 may be capable of operating with one or more air interface standards, communication protocols, modulation types, access types, and/or the like. The client devices 358 include desktop computing systems, notebook computers, mobile phones, smart phones, personal digital assistants, tablets and/or the like.

In an example embodiment, components/modules of the alert reception system 102, the data analysis system 104, the alert validation system 106 and/or the natural language generation system 108 are implemented using standard programming techniques. For example, the alert reception system 102, the data analysis system 104, the alert validation system 106 and/or the natural language generation system 108 may be implemented as a "native" executable running on the processor 303, along with one or more static or dynamic libraries. In other embodiments, the alert reception system 102, the data analysis system 104, the alert validation system 106 and/or the natural language generation system 108 may be implemented as instructions processed by a virtual machine that executes as one of the other programs 330. In general, a range of programming languages known in the art may be employed for implementing such example embodiments, including representative implementations of various programming language paradigms, including but not limited to, object-oriented (e.g., Java, C++, C#, Visual Basic.NET, Smalltalk, and the like), functional (e.g., ML, Lisp, Scheme, and the like), procedural (e.g., C, Pascal, Ada, Modula, and the like), scripting (e.g., Perl, Ruby, Python, JavaScript, VBScript, and the like), and declarative (e.g., SQL, Prolog, and the like).

The embodiments described above may also use synchronous or asynchronous client-server computing techniques. Also, the various components may be implemented using more monolithic programming techniques, for example, as an executable running on a single processor computer system, or alternatively decomposed using a variety of structuring techniques, including but not limited to, multiprogramming, multithreading, client-server, or peer-to-peer, running on one or more computer systems each having one or more processors. Some embodiments may execute concurrently and asynchronously, and communicate using message passing techniques. Equivalent synchronous embodiments are also supported. Also, other functions could be implemented and/or performed by each component/module, and in different orders, and by different components/modules, yet still achieve the described functions.

In addition, programming interfaces to the data stored as part of the alert reception system 102, the data analysis system 104, the alert validation system 106 and/or the natural language generation system 108, such as by using one or more application programming interfaces can be made available by mechanisms such as through application programming interfaces (API) (e.g. C, C++, C#, and Java); libraries for accessing files, databases, or other data repositories; through scripting languages such as XML; or through Web servers, FTP servers, or other types of servers providing access to stored data. The raw input data 110, historical data 112, the domain model 114 and/or the event log 116 may be implemented as one or more database systems, file systems, or any other technique for storing such information, or any combination of the above, including implementations using distributed computing techniques. Alternatively or additionally, the raw input data 110, historical data 112, the domain model 114 and/or the event log 116 may be local data stores but may also be configured to access data from the remote data sources/alert systems 356.

Different configurations and locations of programs and data are contemplated for use with techniques described herein. A variety of distributed computing techniques are appropriate for implementing the components of the illustrated embodiments in a distributed manner including but not limited to TCP/IP sockets, RPC, RMI, HTTP, Web Services (XML-RPC, JAX-RPC, SOAP, and the like). Other variations are possible. Also, other functionality could be provided by each component/module, or existing functionality could be distributed amongst the components/modules in different ways, yet still achieve the functions described herein.

Furthermore, in some embodiments, some or all of the components of the alert reception system 102, the data analysis system 104, the alert validation system 106 and/or the natural language generation system 108 may be implemented or provided in other manners, such as at least partially in firmware and/or hardware, including, but not limited to one or more ASICs, standard integrated circuits, controllers executing appropriate instructions, and including microcontrollers and/or embedded controllers, FPGAs, complex programmable logic devices ("CPLDs"), and the like. Some or all of the system components and/or data structures may also be stored as contents (e.g., as executable or other machine-readable software instructions or structured data) on a computer-readable medium so as to enable or configure the computer-readable medium and/or one or more associated computing systems or devices to execute or otherwise use or provide the contents to perform at least some of the described techniques. Some or all of the system components and data structures may also be stored as data signals (e.g., by being encoded as part of a carrier wave or included as part of an analog or digital propagated signal) on a variety of computer-readable transmission mediums, which are then transmitted, including across wireless-based and wired/cable-based mediums, and may take a variety of forms (e.g., as part of a single or multiplexed analog signal, or as multiple discrete digital packets or frames). Such computer program products may also take other forms in other embodiments. Accordingly, embodiments of this disclosure may be practiced with other computer system configurations.

FIGS. 4-8 illustrate example flowcharts of the operations performed by an apparatus, such as computing system 300 of FIG. 3, in accordance with example embodiments of the present invention. It will be understood that each block of the flowcharts, and combinations of blocks in the flowcharts, may be implemented by various means, such as hardware, firmware, one or more processors, circuitry and/or other devices associated with execution of software including one or more computer program instructions. For example, one or more of the procedures described above may be embodied by computer program instructions. In this regard, the computer program instructions which embody the procedures described above may be stored by a memory 301 of an apparatus employing an embodiment of the present invention and executed by a processor 303 in the apparatus. As will be appreciated, any such computer program instructions may be loaded onto a computer or other programmable apparatus (e.g., hardware) to produce a machine, such that the resulting computer or other programmable apparatus provides for implementation of the functions specified in the flowcharts' block(s). These computer program instructions may also be stored in a non-transitory computer-readable storage memory that may direct a computer or other programmable apparatus to function in a particular manner, such that the instructions stored in the computer-readable storage memory produce an article of manufacture, the execution of which implements the function specified in the flowcharts' block(s). The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowcharts' block(s). As such, the operations of FIGS. 4-8, when executed, convert a computer or processing circuitry into a particular machine configured to perform an example embodiment of the present invention. Accordingly, the operations of FIGS. 4-8 define an algorithm for configuring a computer or processor, to perform an example embodiment. In some cases, a general purpose computer may be provided with an instance of the processor which performs the algorithm of FIGS. 4-8 to transform the general purpose computer into a particular machine configured to perform an example embodiment.

Accordingly, blocks of the flowchart support combinations of means for performing the specified functions and combinations of operations for performing the specified functions. It will also be understood that one or more blocks of the flowcharts', and combinations of blocks in the flowchart, can be implemented by special purpose hardware-based computer systems which perform the specified functions, or combinations of special purpose hardware and computer instructions.

In some example embodiments, certain ones of the operations herein may be modified or further amplified as described below. Moreover, in some embodiments additional optional operations may also be included (some examples of which are shown in dashed lines in FIG. 4). It should be appreciated that each of the modifications, optional additions or amplifications described herein may be included with the operations herein either alone or in combination with any others among the features described herein.

Figure 4:
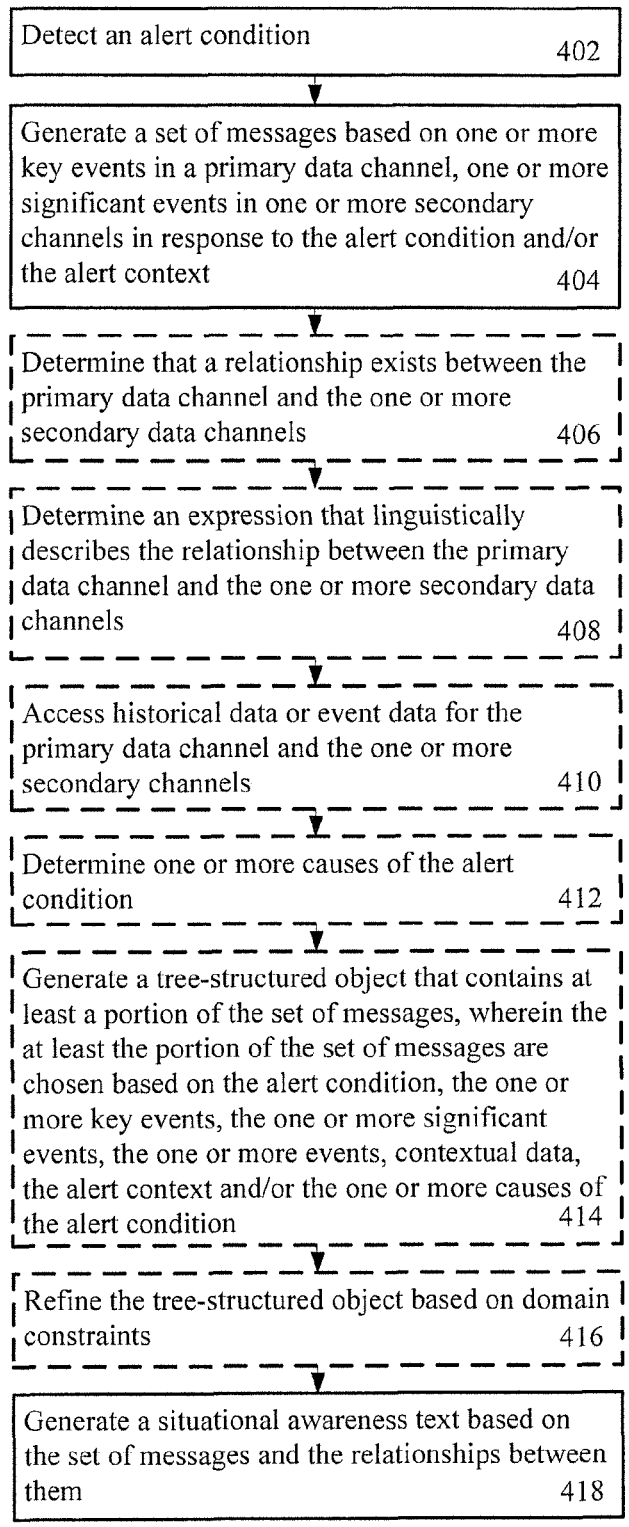

FIG. 4 is a flow chart illustrating an example method for generating a situational analysis text. As is shown in operation 402, an apparatus may include means, such as the alert reception system 102, the data analysis system 104, the processor 303, or the like, for detecting an alert condition. As is shown in operation 404, an apparatus may include means, such as the data analysis system 104, the data interpreter 122, the natural language generation system 108, the processor 303, or the like, for generating a set of messages based on one or more key events in a primary data channel, one or more significant events in one or more related data channels in response to the alert condition, and/or the alert context (e.g. FIG. 6).

As is shown in operation 406, an apparatus may include means, such as the data analysis system 104, the data analyzer 120, the data interpreter 122, the natural language generation system 108, the processor 303, or the like, for determining that a relationship exists between the primary data channel and the one or more related data channels. As is shown in operation 408, an apparatus may include means, such as the data analysis system 104, the data analyzer 120, the data interpreter 122, the natural language generation system 108, the processor 303, or the like, for determining an expression that linguistically describes the relationship between the primary data channel and the one or more related data channels. In some example embodiments, the primary and/or the one or more related data channels comprises high frequency data.

As is shown in operation 410, an apparatus may include means, such as the data analysis system 104, the data analyzer 120, the data interpreter 122, the natural language generation system 108, the processor 303, or the like, or the like, for accessing historical data or event data for the primary data channel and the one or more related data channels. In some example embodiments, the historical data further comprises at least one of previous events, actions taken during a previous instance of the alert condition or results of a previous alert condition. As is shown in operation 412, an apparatus may include means, such as the data analysis system 104, the data analyzer 120, the data interpreter 122, the natural language generation system 108, the domain model 114, the processor 303, or the like, for determining one or more causes of the alert condition. Determining one or more causes of the alert condition may include determining an alert context which is further described with reference to FIG. 6.

As is shown in operation 414, an apparatus may include means, such as the natural language generation system 108, the document planner 130, the processor 303, or the like, for a tree-structured object that contains at least a portion of the set of messages, wherein the at least the portion of the set of messages are chosen based on the alert condition, the one or more key events, the one or more significant events, the one or more events, contextual data, the alert context (e.g. FIG. 6) and/or the one or more causes of the alert condition. As is shown in operation 416, an apparatus may include means, such as the natural language generation system 108, the document planner 130, the processor 303, or the like, for refining the tree-structured object based on domain constraints. The domain constraints may be defined by a domain model, a user or a like. In some example embodiments, the situational analysis text is generated based on a realization of the tree-structured object.

As is shown in operation 418, an apparatus may include means, such as the natural language generation system 108, the document planner 130, the microplanner 132, the processor 303, or the like, for generating a situational analysis text based on the set of messages and the relationships between them. In some example embodiments, the situational analysis text is configured to linguistically express the one or more key events, the one or more significant events, and the relationships between the one or more key events and the one or more significant events. The situational analysis text is further configured to express the relationships between the alert condition and the one or more key events and the one or more significant events. In some examples, the situational analysis text is further configured to express a proximate cause of the alert condition or an explanation of a diagnosis of the alert condition. Alternatively or additionally, in some example embodiments, the situational analysis text is further configured to comprise at least one of coherent text describing the alert condition, one or more events, and a history of the alert condition or related alert conditions.

Figure 5:
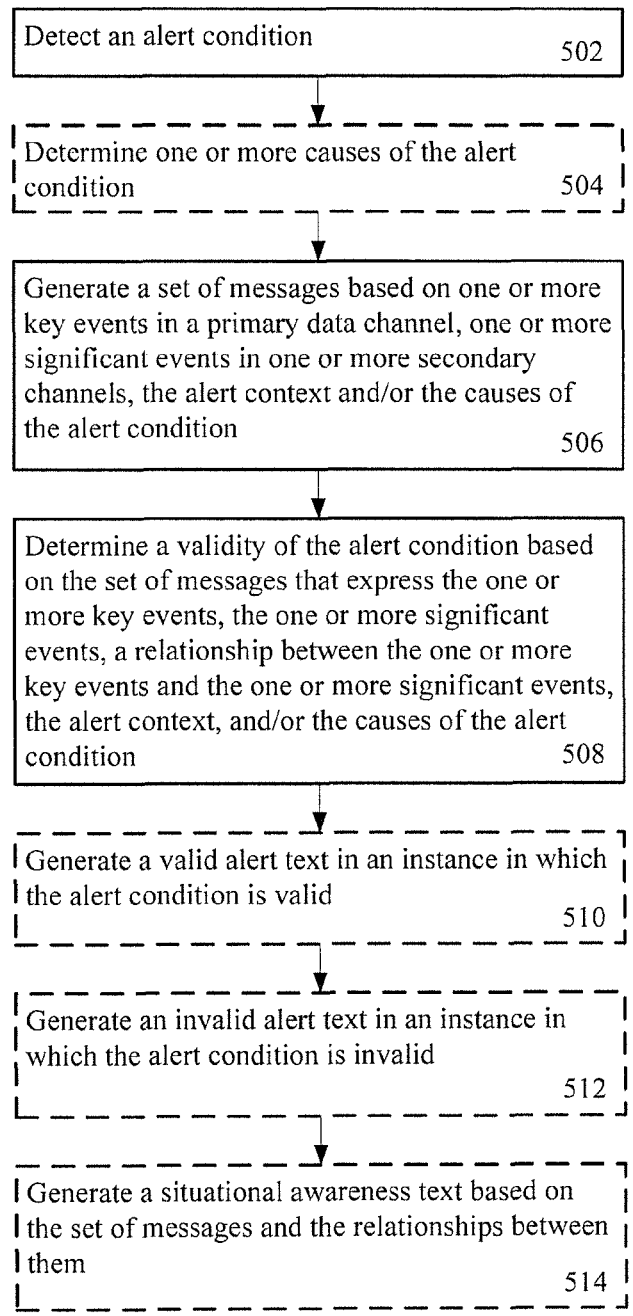

FIG. 5 is a flow chart illustrating an example method for performing alert validation. As is shown in operation 502, an apparatus may include means, such as the alert reception system 102, the data analysis system 104, the processor 303, or the like, for detecting an alert condition. As is shown in operation 506, an apparatus may include means, such as the data analysis system 104, the data interpreter 122, the natural language generation system 108, the domain model 114, the processor 303, or the like, for determining one or more causes of the alert condition. Determining one or more causes of the alert condition may include determining an alert context which is further described with reference to FIG. 6.

As is shown in operation 506, an apparatus may include means, such as the data analysis system 104, the data interpreter 122, the natural language generation system 108, the processor 303, or the like, for generating a set of messages based on one or more key events in a primary data channel, one or more significant events in one or more secondary channels, the alert context (e.g. FIG. 6) and/or the causes of the alert condition. As is shown in operation 508, an apparatus may include means, such as the data analysis system 104, the alert validation system 106, the natural language generation system 108, the processor 303, or the like, for determining a validity of the alert condition based on the set of messages that express the one or more key events, the one or more significant events, a relationship between the one or more key events and the one or more significant events, the alert context (e.g. FIG. 6) and/or the causes of the alert condition.

As is shown in operation 510, an apparatus may include means, such the data analysis system 104, the alert validation system 106, the natural language generation system 108, the processor 303, or the like, for generating a valid trigger event text in an instance in which the alert condition is valid. As is shown in operation 512, an apparatus may include means, such as the data analysis system 104, the alert validation system 106, the natural language generation system 108, the processor 303, or the like, or the like, for generating an invalid trigger event text in an instance in which the alert condition is invalid. In some example embodiments, the trigger event text is configured to provide a rational for the validity determination and context information generated based on the one or more key events and the one or more significant events. As is shown in operation 514, an apparatus may include means, such as the natural language generation system 108, the document planner 130, the microplanner 132, the realizer 134, the processor 303, or the like, for generating a situational analysis text based on the set of messages and the relationships between them.

FIG. 6 is a flow chart illustrating an example method for determining a context an alert condition. As is shown in operation 602, an apparatus may include means, such as the alert reception system 102, the data analysis system 104, the processor 303, or the like, for determining whether the alert condition is an intermittent alert condition. In an instance in which the alert condition is an intermittent alert condition a message may be generated that is configured to summarize such a behavior. As is shown in operation 604, an apparatus may include means, such as the alert reception system 102, the data analysis system 104, the processor 303, or the like, for determining whether there is a previous instance of the alert condition on the machine apparatus. In an instance in which there is a previous instance of the alert condition on the machine apparatus, a message may be generated that is configured to summarize the previous instances. As is shown in operation 606, an apparatus may include means, such as the alert reception system 102, the data analysis system 104, the processor 303, or the like, for determining the actions taken in an instance in which a previous instance of the alert condition and/or a previous intermittent alert condition has been determined. In an instance in which previous actions were taken, a message may be generated that is configured to summarize the previous actions. As is shown in operation 608, an apparatus may include means, such as the alert reception system 102, the data analysis system 104, the processor 303, or the like, for determining whether there is at least one of another active alert condition or a maintenance request on the machine apparatus. In an instance in which there is at least one of another active alert condition or a maintenance request on the machine apparatus a message may be generated that is configured to summarize the instances. As is shown in operation 610, an apparatus may include means, such as the alert reception system 102, the data analysis system 104, the processor 303, or the like, for determining whether there is at least one of an another active alert condition or a maintenance request on another related machine apparatus. In an instance in which there is at least one of an another active alert condition or a maintenance request on another related machine apparatus a message may be generated that is configured to summarize the instances.

Figure 7:
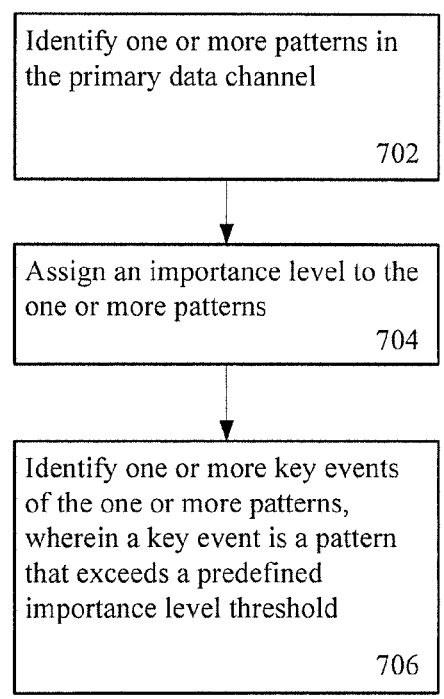

FIG. 7 is a flow chart illustrating an example method determining one or more key events in a primary data channel. As is shown in operation 702, an apparatus may include means, such as the data analysis system 104, the data analyzer 120, the data interpreter 122, the processor 303, or the like, for identifying one or more patterns in the primary data channel. As is shown in operation 704, an apparatus may include means, such as the data analysis system 104, the data analyzer 120, the data interpreter 122, the processor 303, or the like, for assigning an importance level to the one or more patterns. As is shown in operation 706, an apparatus may include means, such as the data analysis system 104, the data analyzer 120, the data interpreter 122, the processor 303, or the like, for identifying one or more key events of the one or more patterns, wherein a key event is a pattern that exceeds a predefined importance level threshold.

Figure 8:
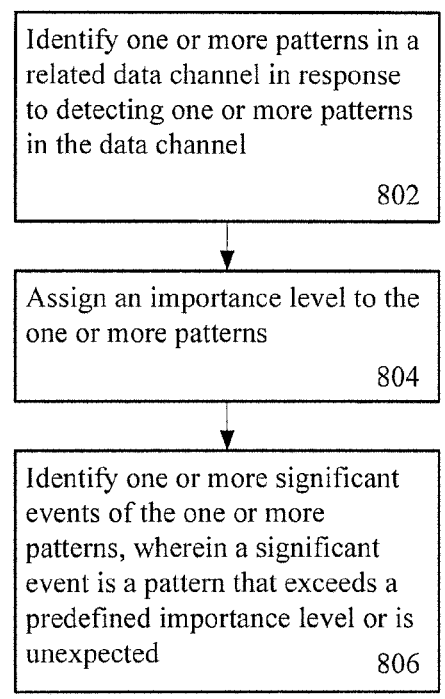

FIG. 8 is a flow chart illustrating an example method determining one or more significant events in a related data channel. As is shown in operation 802, an apparatus may include means, such as the data analysis system 104, the data analyzer 120, the data interpreter 122, the processor 303, or the like, for identifying one or more patterns in a related data channel in response to detecting one or more patterns in the data channel. As is shown in operation 804, an apparatus may include means, such as the data analysis system 104, the data analyzer 120, the data interpreter 122, the processor 303, or the like, for assigning an importance level to the one or more patterns. As is shown in operation 806, an apparatus may include means, such as the data analysis system 104, the data analyzer 120, the data interpreter 122, the processor 303, or the like, for identifying one or more significant events of the one or more patterns, wherein a significant event is a pattern that exceeds a predefined importance level or is unexpected.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method for verifying a cause of an alert condition associated with one or more data channels, the method comprising:
   determining, using at least one processor, at least one key event in each of one or more primary data channels, wherein the at least one key event indicates the alert condition;
   identifying, using the at least one processor and a diagnostic model, one or more possible causes of the alert condition;
   determining, using the at least one processor and the diagnostic model, one or more secondary data channels to verify a cause of the alert condition of the one or more possible causes;
   verifying the cause of the alert condition; and
   generating, using the at least one processor, an alert validation text, wherein the alert validation text is configured to linguistically express the at least one key event and the cause of the alert condition.

2. The method of claim 1, wherein the one or more secondary data channels are related to the one or more primary data channels.

3. The method of claim 1, wherein the alert validation text is further configured to linguistically express a recommended response to the alert condition based at least on the cause of the alert condition.

4. The method of claim 1, herein identifying one or more possible causes of the alert condition comprises generating an alert context.

5. The method of claim 4, further comprising:
   generating an alert context based on one or more of a determination of whether the alert condition is an intermittent alert condition, a determination of whether there is at least one previous instance of the alert condition on an apparatus that is currently experiencing the alert condition, a determination of one or more actions taken with respect to the previous instance of the alert condition in an instance in which there is at least one previous instance of the alert condition, a determination of whether there is at least one of another active alert condition or a maintenance request on the apparatus, or a determination of whether there is at least one of another active alert condition or another maintenance request on a related apparatus.

6. The method of claim 1, wherein verifying the cause of the alert condition comprises evaluating raw data in the one or more secondary data channels.

7. The method of claim 1, wherein the one or more secondary data channels are identified as related to the one or more primary data channels based in part on a detection of a significant event in raw data in the one or more secondary data channels.

8. The method of claim 1, wherein the one or more secondary data channels are selected based on a rule language that is configured to qualitatively specify expected relationships between data channels.

9. An apparatus for verifying a cause of an alert condition associated with one or more data channels, the apparatus comprising at least one processor and at least one non-transitory memory including program code, the at least one memory and the program code being configured to, with the at least one processor, cause the apparatus to:
- determine at least one key event in each of one or more primary data channels, wherein the at least one key event indicates the alert condition;
- identify, using a diagnostic model, one or more possible causes of the alert condition;
- determine, using the diagnostic model, one or more secondary data channels to verify a cause of the alert condition of the one or more possible causes;
- verify the cause of the alert condition; and
- generate an alert validation text, wherein the alert validation text is configured to linguistically express the at least one key event and the cause of the alert condition.

10. The apparatus of claim 9, wherein the one or more secondary data channels are related to the one or more primary data channels.

11. The apparatus of claim 9, wherein the alert validation text is further configured to linguistically express a recommended response to the alert condition based at least on the cause of the alert condition.

12. The apparatus of claim 9, wherein identifying one or more possible causes of the alert condition comprises generating an alert context.

13. The apparatus of claim 12, further caused to:
- generate an alert context based on one or more of a determination of whether the alert condition is an intermittent alert condition, a determination of whether there is at least one previous instance of the alert condition on an apparatus that is currently experiencing the alert condition, a determination of one or more actions taken with respect to the previous instance of the alert condition in an instance in which there is at least one previous instance of the alert condition, a determination of whether there is at least one of another active alert condition or a maintenance request on the apparatus, or a determination of whether there is at least one of another active alert condition or another maintenance request on a related apparatus.

14. The apparatus of claim 9, wherein verifying the cause of the alert condition comprises evaluating raw data in the one or more secondary data channels.

15. The apparatus of claim 9, wherein the one or more secondary data channels are identified as related to the one or more primary data channels based in part on a detection of a significant event in raw data in the one or more secondary data channels.

16. The apparatus of claim 1, wherein the one or more secondary data channels are selected based on a rule language that is configured to qualitatively specify expected relationships between data channels.

* * * * *